US007216802B1

(12) United States Patent
De La Huerga

(10) Patent No.: US 7,216,802 B1
(45) Date of Patent: May 15, 2007

(54) METHOD AND APPARATUS FOR VERIFYING INFORMATION

(76) Inventor: Carlos De La Huerga, 9190 N. Upper River Rd., Milwaukee, WI (US) 53217

( * ) Notice: Subject to any disclaimer, the term of this patent is extended or adjusted under 35 U.S.C. 154(b) by 0 days.

(21) Appl. No.: 09/426,553

(22) Filed: Oct. 22, 1999

Related U.S. Application Data

(63) Continuation-in-part of application No. 08/955,475, filed on Oct. 21, 1997, now Pat. No. 6,032,155.

(51) Int. Cl.
*G06K 5/00* (2006.01)
(52) U.S. Cl. .................................. 235/380; 235/382
(58) Field of Classification Search ................ 235/380, 235/382, 385; 705/22, 28
See application file for complete search history.

(56) References Cited

U.S. PATENT DOCUMENTS

| | | |
|---|---|---|
| 3,227,127 A | 1/1966 | Gayle |
| 3,762,601 A | 10/1973 | McLaughlin |
| 4,094,561 A | 6/1978 | Wolff et al. |
| 4,207,992 A | 6/1980 | Brown |
| 4,360,125 A | 11/1982 | Martindale |
| 4,368,988 A | 1/1983 | Tahara et al. |
| 4,384,288 A | 5/1983 | Walton |
| 4,437,579 A | 3/1984 | Obland |
| 4,476,381 A | 10/1984 | Rubin |
| 4,483,626 A | 11/1984 | Noble |
| 4,504,153 A | 3/1985 | Schollmeyer et al. |
| 4,526,474 A | 7/1985 | Simon |
| 4,546,901 A | 10/1985 | Buttarazzi |
| 4,573,606 A | 3/1986 | Lewis et al. |
| 4,575,621 A | 3/1986 | Dreifus |
| 4,598,275 A | 7/1986 | Ross et al. |
| 4,616,316 A | 10/1986 | Hanpeter et al. |
| 4,617,557 A | 10/1986 | Gordon |
| 4,626,105 A | 12/1986 | Miller |
| 4,664,289 A | 5/1987 | Shimizu et al. |

(Continued)

FOREIGN PATENT DOCUMENTS

GB 2154344 9/1985

OTHER PUBLICATIONS

Paul Lavin, "Small but perfectly informed Will a Java Ring become the next must-have fashion accessory?" The Independent, London, Apr. 7, 1998.

(Continued)

*Primary Examiner*—Karl D. Frech
(74) *Attorney, Agent, or Firm*—Quarles & Brady LLP

(57) ABSTRACT

A system and method for verifying information and controlling a response function when two or more pieces of information correspond to each other. The system includes an information device and an identification device. The information device has identification information stored therein. The identification device has identification information stored therein or thereon. The information device obtains the identification information from the identification device and compares it to the identification information in the information device. If the identification information corresponds, the information device provides a response signal. The response signal may control a locking mechanism for a container to which the information device is attached or provide an audible or visual indication. The system and method may be used for controlling the administration of prescribed medication to a patient or in other medical or non-medical applications.

114 Claims, 23 Drawing Sheets

U.S. PATENT DOCUMENTS

| | | |
|---|---|---|
| 4,674,651 A | 6/1987 | Scidmore et al. |
| 4,674,652 A | 6/1987 | Aten et al. |
| 4,694,284 A | 9/1987 | Leveille et al. |
| 4,695,954 A | 9/1987 | Rose et al. |
| 4,717,261 A | 1/1988 | Kita et al. |
| 4,725,997 A | 2/1988 | Urquhart et al. |
| 4,730,849 A | 3/1988 | Siegel |
| 4,732,411 A | 3/1988 | Siegel |
| 4,733,362 A | 3/1988 | Haraguchi |
| 4,733,797 A | 3/1988 | Haber |
| 4,785,969 A | 11/1988 | McLaughlin |
| 4,811,764 A | 3/1989 | McLaughlin |
| 4,812,985 A * | 3/1989 | Hambrick et al. .......... 700/215 |
| 4,817,050 A | 3/1989 | Komatsu et al. |
| 4,823,982 A | 4/1989 | Aten et al. |
| 4,835,372 A | 5/1989 | Gombrich et al. |
| 4,839,806 A | 6/1989 | Goldfischer et al. |
| 4,847,764 A | 7/1989 | Halvorson |
| 4,850,009 A | 7/1989 | Zook et al. |
| 4,857,713 A | 8/1989 | Brown |
| 4,857,716 A | 8/1989 | Gombrich et al. |
| 4,885,571 A | 12/1989 | Pauley et al. |
| 4,898,578 A | 2/1990 | Rubalcaba, Jr. |
| 4,911,327 A | 3/1990 | Shepherd et al. |
| 4,916,441 A | 4/1990 | Gombrich |
| 4,939,705 A | 7/1990 | Hamilton et al. |
| 4,952,928 A | 8/1990 | Carroll et al. |
| 4,953,745 A | 9/1990 | Rowlett, Jr. |
| 4,967,928 A | 11/1990 | Carter |
| 4,971,221 A | 11/1990 | Urquhart et al. |
| 4,973,944 A | 11/1990 | Maletta |
| 4,978,335 A | 12/1990 | Arthur, III |
| 4,980,671 A | 12/1990 | McCurdy |
| 4,984,709 A | 1/1991 | Weinstein |
| 5,012,229 A | 4/1991 | Lennon et al. |
| 5,014,875 A | 5/1991 | McLaughlin et al. |
| 5,032,823 A | 7/1991 | Bower et al. |
| 5,038,023 A * | 8/1991 | Saliga .................. 235/385 |
| 5,047,948 A | 9/1991 | Turner |
| 5,048,870 A | 9/1991 | Mangini et al. |
| 5,071,168 A | 12/1991 | Shamos |
| 5,075,670 A | 12/1991 | Bower et al. |
| 5,078,683 A | 1/1992 | Sancoff et al. |
| 5,088,056 A | 2/1992 | McIntosh et al. |
| 5,099,463 A | 3/1992 | Lloyd et al. |
| 5,104,374 A | 4/1992 | Bishko et al. |
| 5,115,223 A | 5/1992 | Moody |
| 5,161,199 A | 11/1992 | David |
| 5,164,575 A * | 11/1992 | Neeley et al. ......... 235/472.01 |
| 5,166,498 A | 11/1992 | Neeley |
| 5,176,285 A | 1/1993 | Shaw |
| 5,181,189 A | 1/1993 | Hafner |
| 5,193,855 A | 3/1993 | Shamos |
| 5,202,929 A | 4/1993 | Lemelson |
| 5,204,670 A | 4/1993 | Stinton |
| 5,208,762 A | 5/1993 | Charhut et al. |
| 5,213,232 A | 5/1993 | Kraft et al. |
| 5,233,571 A | 8/1993 | Wirtschafter |
| 5,256,157 A | 10/1993 | Samiotes et al. |
| 5,272,318 A | 12/1993 | Gorman |
| 5,287,414 A * | 2/1994 | Foster ................... 382/100 |
| 5,289,157 A | 2/1994 | Rudick et al. |
| 5,303,214 A * | 4/1994 | Kulakowski et al. ...... 369/30.3 |
| 5,313,052 A * | 5/1994 | Watanabe et al. .......... 235/375 |
| 5,313,439 A | 5/1994 | Albeck |
| 5,317,506 A | 5/1994 | Coutre et al. |
| 5,319,363 A | 6/1994 | Welch et al. |
| 5,319,711 A | 6/1994 | Servi |
| 5,337,919 A | 8/1994 | Spaulding et al. |
| 5,347,453 A | 9/1994 | Maestre |
| 5,348,061 A | 9/1994 | Riley et al. |
| 5,381,487 A | 1/1995 | Shamos |
| 5,392,952 A | 2/1995 | Bowden |
| 5,398,220 A | 3/1995 | Baker |
| 5,401,059 A | 3/1995 | Ferrario |
| 5,405,048 A | 4/1995 | Rogers et al. |
| 5,408,443 A | 4/1995 | Weinberger |
| 5,408,655 A | 4/1995 | Oren et al. |
| 5,412,372 A | 5/1995 | Parkhurst et al. |
| 5,431,299 A | 7/1995 | Brewer et al. |
| 5,445,621 A | 8/1995 | Poli et al. |
| 5,455,851 A | 10/1995 | Chaco et al. |
| 5,460,294 A | 10/1995 | Williams |
| 5,472,113 A | 12/1995 | Shaw |
| 5,477,511 A | 12/1995 | Englehardt |
| 5,478,991 A * | 12/1995 | Watanabe et al. .......... 235/375 |
| 5,480,062 A | 1/1996 | Rogers et al. |
| 5,491,482 A | 2/1996 | Dingwall et al. |
| 5,491,774 A | 2/1996 | Norris et al. |
| 5,493,805 A | 2/1996 | Penuela et al. |
| 5,499,626 A | 3/1996 | Willham et al. |
| 5,502,445 A | 3/1996 | Dingwall et al. |
| 5,502,944 A | 4/1996 | Kraft et al. |
| 5,504,474 A | 4/1996 | Libman et al. |
| 5,508,499 A | 4/1996 | Ferrario |
| 5,511,000 A | 4/1996 | Kaloi et al. |
| 5,512,879 A | 4/1996 | Stokes |
| 5,512,880 A | 4/1996 | Abrams et al. |
| 5,519,808 A | 5/1996 | Benton, Jr. et al. |
| 5,522,525 A | 6/1996 | McLaughlin et al. |
| 5,525,969 A | 6/1996 | LaDue |
| 5,527,289 A | 6/1996 | Foster et al. |
| 5,532,705 A | 7/1996 | Hama |
| 5,541,580 A | 7/1996 | Gerston et al. |
| 5,541,583 A | 7/1996 | Mandelbaum |
| 5,548,566 A | 8/1996 | Barker |
| 5,548,660 A | 8/1996 | Lemelson |
| 5,564,005 A | 10/1996 | Weber et al. |
| 5,593,267 A | 1/1997 | McDonald et al. |
| 5,594,786 A | 1/1997 | Chaco et al. |
| 5,602,963 A | 2/1997 | Bissonnette et al. |
| 5,609,268 A | 3/1997 | Shaw |
| 5,609,716 A | 3/1997 | Mosher, Jr. |
| 5,612,675 A | 3/1997 | Jennings et al. |
| 5,621,384 A | 4/1997 | Crimmins et al. |
| 5,623,242 A | 4/1997 | Dawson, Jr. et al. |
| 5,627,520 A | 5/1997 | Grubbs et al. |
| 5,629,981 A | 5/1997 | Nerlikar |
| 5,642,906 A | 7/1997 | Foote et al. |
| 5,643,212 A | 7/1997 | Coutre et al. |
| 5,646,912 A | 7/1997 | Cousin |
| 5,650,766 A | 7/1997 | Burgmann |
| 5,659,741 A | 8/1997 | Eberhardt |
| 5,660,176 A | 8/1997 | Lliff |
| 5,671,362 A * | 9/1997 | Cowe et al. ................ 705/28 |
| 5,678,925 A | 10/1997 | Garmaise et al. |
| 5,681,285 A | 10/1997 | Ford et al. |
| 5,689,567 A | 11/1997 | Miyauchi |
| 5,713,856 A | 2/1998 | Eggers et al. |
| RE35,743 E | 3/1998 | Pearson |
| 5,732,401 A | 3/1998 | Conway |
| 5,742,233 A | 4/1998 | Hoffman et al. |
| 5,745,366 A | 4/1998 | Higham et al. |
| 5,768,813 A | 6/1998 | Reboul et al. |
| 5,771,001 A | 6/1998 | Cobb |
| 5,772,635 A | 6/1998 | Dastur et al. |
| 5,781,442 A | 7/1998 | Engleson et al. |
| 5,782,805 A | 7/1998 | Meinzer et al. |
| 5,793,290 A | 8/1998 | Eagleson et al. |
| 5,826,217 A | 10/1998 | Lerner |
| 5,833,599 A | 11/1998 | Schrier et al. |
| 5,839,836 A | 11/1998 | Yuyama et al. |
| 5,851,186 A | 12/1998 | Wood et al. |
| 5,852,590 A | 12/1998 | de la Huerga |

| | | |
|---|---|---|
| 5,852,911 A | 12/1998 | Yuyama et al. |
| 5,855,395 A | 1/1999 | Foote et al. |
| 5,868,669 A | 2/1999 | Lliff |
| 5,877,675 A | 3/1999 | Rebstock et al. |
| 5,877,742 A | 3/1999 | Klink |
| 5,882,338 A | 3/1999 | Gray |
| 5,883,370 A | 3/1999 | Walker et al. |
| 5,883,576 A | 3/1999 | de la Huerga |
| 5,924,074 A | 7/1999 | Evans |
| 5,936,529 A | 8/1999 | Reisman et al. |
| 5,945,651 A | 8/1999 | Chorosinski et al. |
| 5,953,682 A * | 9/1999 | McCarrick et al. ............ 702/45 |
| 5,954,700 A | 9/1999 | Kovelman |
| 5,960,085 A | 9/1999 | de la Huerga |
| 5,970,388 A | 10/1999 | Will |
| 5,979,757 A | 11/1999 | Tracy et al. |
| 5,980,501 A | 11/1999 | Gray |
| 5,997,476 A | 12/1999 | Brown |
| 6,019,745 A | 2/2000 | Gray |
| 6,032,155 A | 2/2000 | de la Huerga |
| 6,036,231 A | 3/2000 | Foote et al. |
| 6,070,148 A | 5/2000 | Mori et al. |
| 6,070,761 A | 6/2000 | Bloom et al. |
| 6,104,295 A | 8/2000 | Gaisser et al. |
| 6,110,152 A | 8/2000 | Kovelman |
| 6,140,936 A | 10/2000 | Armstrong |
| 6,144,303 A | 11/2000 | Federman |
| 6,169,707 B1 | 1/2001 | Newland |
| 6,219,587 B1 | 4/2001 | Ahlin et al. |
| 6,255,951 B1 | 7/2001 | de la Huerga |
| 6,259,654 B1 | 7/2001 | de la Huerga |
| 6,263,330 B1 | 7/2001 | Bessette |
| 6,283,761 B1 | 9/2001 | Joao |
| 6,294,999 B1 | 9/2001 | Yarin et al. |
| 6,317,390 B1 | 11/2001 | Cardoza |
| 6,324,123 B1 | 11/2001 | Durso |
| 6,346,886 B1 | 2/2002 | de la Huerga |
| 6,539,281 B2 | 3/2003 | Wan et al. |
| 6,745,941 B1 * | 6/2004 | Vega ........................... 235/382 |

OTHER PUBLICATIONS

"Medical alerty systems," The University of California Berkley Wellness Letter, vol. 7, No. 1, p. 1, Oct. 1990.

"Surgical patients carry records on wristband", USA Today, vol. 126, No. 2631, p. 7, Dec. 1997.

Magic Medicine Cabinet: A Situated Portal for Consumer Healthcare, HUC '99, Dadong Wan, Center for Strategic Technology Research Accenture, Morthbrook IL (4 pages).

* cited by examiner

| | |
|---|---|
| 500 | Memory Contents -- Information Device 10 |
| 504 | Information Device Data Elements |
| 505 | Serial Number of Information Device |
| 506 | End of Life for Battery |
| 507 | Communication Encryption Codes |
| 508 | Number of Compartments |
| | Information Received from Dispensing System 200, 280 for Compartment *i* |
| 520 | Selected Patient Information |
| 540 | Selected Prescribed Medication Dose Information |
| 560 | Predetermined Healthcare Worker Information |
| 580 | Dispensed Medication Information |
| 600 | Medication Report Components |
| | Information Received from Patient Identification Device 300 for Compartment *i* |
| 621 | Specific Patient Information |
| | Information Received from Healthcare Worker Identification Device 320 for Compartment *i* |
| 681 | Administering Healthcare Worker Information |
| 621 | Specific Patient Information |
| | Information Received from Patient Room Workstation 350 or Computer Peripheral Device 355 for Compartment *i* |
| 621 | Specific Patient Information |
| | Information Created when Container 100 opened for Compartment *i* |
| 640 | Consumption Information: |
| 642 | Consumption Tiem Information/Date and time portable container opened |
| 643 | Amount of Medication offered to Patient |
| 644 | Amount of Medication Patient Consumed |
| 660 | Final Transaction Medication Report |

Figure 17

| 700 | Patient Medication Information -- Dispensing Workstation 200, 280 |
|---|---|
| 520 | Selected Patient Information |
| 521 |     Patient Identification Number |
| 522 |     Patient Name |
| 523 |     Admitting Physician |
| 524 |     Patient Room Number |
| 525 |     Patient Blood Type |
| | |
| 540 | Selected Prescribed Medication Dose Information for each Medication Prescribed |
| 541 |     Medication Type Prescribed |
| 542 |     Medication Quantity Prescribed |
| 543 |     Dosing Times |
| 544 |     Identification of Physician Prescribing Medication |
| | |
| 560 | Predetermined Healthcare Worker Information |
| 561 |     Responsibilities/Title Of Healthcare Worker Allowed to Give Medication |
| 562 |     Healthcare Worker Identification Number(s) Allowed to Give Medication |
| 563 |     Healthcare Worker Name(s) Allowed to Give Medication |
| 564 |     List of Patients Under Care of each Healthcare Worker |

Figure 18

| 580 | Dispensed Medication Information -- Dispensing Workstation 200, 280 |
|---|---|
| 581 | Medication Information |
| 582 |     Date and Time Medication Dispensed |
| 583 |     Identification of Healthcare Worker who dispensed Medication |
| 584 |     Type and Quantity Actually Dispensed |
| 600 | Medication Report Components |
| 720 |     Medication Report |
| 724 |     Universal Record Locator |

Figure 19

| 620 | Memory Contents -- patient identification device 300 |
|---|---|
| 621 | Specific Patient Information |
| 622 |     Patient Identification Number |
| 623 |     Patient Name |
| 624 |     List of Medications to which Patient is Allergic |
| 625 |     Admitting Physician |
| 626 |     Patient Blood Type |

Figure 20

| 680 | Memory Contents -- Healthcare Worker Identification Device 320 |
|---|---|
| 681 | Administering Healthcare Worker Information |
| 682 |     Responsibilities/Title |
| 683 |     Identification Number |
| 684 |     Name |
| 685 |     List of Patients Under Care of Healthcare Worker |
| | Information Received from patient identification device 300 |
| 621 | Specific Patient Information |
| | Information Received from Information Device 10 |
| 660 | Final Medication Transaction Report |

Figure 21

| 690 | Memory Contents -- Patient Room Information Workstation 350 or Computer Peripheral Device 355 |
|---|---|
| 621 | Specific Patient Information |
| | Information Received from Information Device 10 |
| 660 | Final Medication Transaction Report |

Figure 22

| 660 | Final Medication Transaction Report |
|---|---|
| 520 | Selected Predetermined Patient Information |
| 540 | Selected Prescribed Medication Dose Information |
| 560 | Predetermined Healthcare Worker Information |
| 580 | Dispensed Medication Information |
| 621 | Specific Patient Information |
| 680 | Administering Healthcare Worker Information |
| 640 | Consumption Information: |
| 670 | Medication Report Components |
| 730 |     Medication Report |
| 734 |     Universal Record Locator |

Figure 23

```
<html>
<body>
<a href="http://hww.st._mary.springfield/demographics/987654321/19_May_1996">
ID: 987654321</a><br>
Date: 13:59 19-May-1996<br>
Report type: Medication Administration<br>
Patient ID Verified: YES<br>
<br>
Medication Given:<br>
Penicillin          100mg         2 capsules<br>
Tylenol w/Codeine   200mg         1 capsules<br>
<br>
Given by: XXXXXX,  at: HH:MM  DD/MM/YYYY<br>
Dispensed by: Sam W. Johnston, R.N.,  at: 13:42 19-May-1996<br>
<br>
ID Device Serial Number: 1265338<br>
</html>
```

— 720
— 726
— 728

Figure 24 hww.st_mary.springfield/medication/given/987654321/DD-MM-YYYY/HH-MM — 724

```
<html>
<body>
<a href="http://hww.st_mary.springfield/demographics/987654321/19_May_1996">
ID: 987654321</a><br>
Date: 13:59 19-May-1996<br>
Report type: Medication Administration<br>
Patient ID Verified: YES<br>
<br>
Medication Given:<br>
Penicillin                100mg         2 capsules<br>
Tylenol w/Codeine    200mg         1 capsules<br>
<br>
Given by: Mary T. Adamson, R.N.,   at: 13:59 19-May-1996<br>
Dispensed by: Sam W. Johnston, R.N.,   at: 13:42 19-May-1996<br>
<br>
ID Device Serial Number: 1265338<br>
</html>
```

Figure 26

```
hww.st_mary.springfield/medication/given/987654321/19_May_1996/13:42
```

Figure 27

```
ID: 987654321
Date: 13:59 19-May-1996
Report type: Medication Administration
Patient ID Verified: YES Medication Given:
Penicillin                   100mg        2 capsules
Tylenol w/Codeine     200mg        1 capsules Given by: Mary T. Adamson, R.N.,   at: 13:59 19-May-1996
Dispensed by: Sam W. Johnston, R.N.,   at: 13:42 19-May-1996

ID Device Serial Number: 1265338
```

Figure 28

METHOD AND APPARATUS FOR VERIFYING INFORMATION

CROSS-REFERENCES TO RELATED APPLICATIONS

This application is a continuation-in-part of application Ser. No. 08/955,475, filed Oct. 21, 1997 now U.S. Pat. No. 6,032,155.

TECHNICAL FIELD OF THE INVENTION

This invention relates generally to a method and apparatus for tracking and verifying different pieces of information, including the whereabouts of items, who is entitled to have access to the items, products these items can be applied to, and processes these items can be used with. More particularly, this invention relates to a method and apparatus for dispensing a prescribed dose of medication, tracking and verifying that the medication is administered to a specific patient, automatically recording the time the medication is dispensed, the time the medication is administered, the type and amount of medication being administered, identifying the health care worker administering the medication, and returning this information to a hospital or pharmacy database.

BACKGROUND OF THE INVENTION

There are many instances where individuals wish to transport items between locations and track the whereabouts of the items, who is entitled to have access to the items, and other pertinent information. For example, medication prescribed by a physician in a hospital for a patient can be dispensed either manually by a pharmacist or by a unit dose dispensing system in the pharmacy or placed at various locations in the hospital for nurses to use. In the case of manual dispensing, a medication order is sent to the pharmacy where the correct medication is selected or formulated. The medication is then placed in a container, plastic bag, or envelope which is in turn labeled with identification information specifying the patient that is to receive the medication as well as information about the medication dispensed. Such labeling can be achieved by the use of a marking pen or a computer printer adhesive label.

A variety of devices have been invented and several placed in commercial production for the dispensing of unit dosages of medication. These systems are often designed to be placed in a variety of locations in a hospital for local and convenient dispensing of medications. A key advantage of these systems is a reduction in time and labor in the delivery of prescribed medication to a patient. Without such systems, each prescribed medication must be dispensed by the central hospital pharmacy, labeled, and transported to the nurses station near the patient's room. This process must be done 24 hours a day and the dispensing must be done in anticipation of when each new dosage is due with an allowance for time spent in transit. Unit dosage dispensing systems usually have a tray or cartridge that is loaded with multiple dosages of medication by the central pharmacy. This tray or cartridge is then carried to the unit dosage dispensing system where it is inserted, along with information regarding the medication in the tray or cartridge. This information usually includes the medication name and the number of doses contained. When a patient is to receive medication the nurse usually must use a mechanical key, an electronic key, or a computer password to gain access to the dispensing process. The nurse will identify the medication and may identify the patient to receive the medication. The dispensing system then locates the correct tray or cartridge containing the desired medication and then removes one or more doses of the medication as required, typically delivering them to a drawer or door that the nurse may open to remove the medication.

After dispensing the nurse carries the medication to the patient for consumption. The dispensing system can keep track of the date and time when the medication was dispensed, for which patient it was for, and possibly the nurse to whom it was dispensed. However, the dispensing system cannot determine if the medication was in fact given, if it was given later, who gave it to the patient, or if it was given to the correct patient.

Several studies have documented that most medications in a hospital are given to the correct patient. However, the small percentage of medications that are given to the wrong patient is cause for great concern. This can happen if a patient is moved from one room to another and a new patient is now in the former patient's bed. Occasionally, the former patient's name may be left written on a board near the bed or by the doorway. While nurses are suppose to verify the patient's name or identification number written on a bracelet each time they administer a medication, this may not always happen. The nurse may receive a call to go to an emergency while giving a medication and thus be rushed, the patient may be unable to speak to identify themselves, or the nurse may not want to disturb a patient who is sleeping. Errors in giving medication to the wrong patient can cause a variety of reactions that can sometimes lead to death.

To track when a patient was given medication and who gave it, hospitals employ either manual or computerized recording systems. Manual systems are time consuming and can cause errors in patient billing. Even with computerized record systems, the nurse must spend some amount of time entering and verifying the information. It is claimed that within a hospital that over 60% of all expenses are related to nursing, and of that nearly half of this is for nurses to fill out paperwork and write observations. With continuing efforts to control the rising cost of providing health care, hospitals need to explore all methods possible to reduce nurse time spent away from directly caring for patients.

Problems such as these can occur in other situations, both in hospital settings and elsewhere. For example, hospital personnel may want to store the personal belongings of a particular patient while the patient is receiving treatment and need to identify the belongings so that they are returned to the appropriate patient. Similarly, when medical personnel desire to dispense fluid medication, either in the form of an intravenous solution or medication to be taken orally, they must keep track of how much and what type of fluid is being dispensed and which patients have received their medication. In each of these cases, it can be very time consuming to write down the type and quantity of substances being identified, who is accessing the substances, what time the transaction is taking place and other important information in order to ensure that the task is being performed correctly.

Problems such as these can go far beyond the medical field. In the manufacturing industry, for instance, it is often important to keep adequate records of individual components. For example, if a particular prototype device or key part is being transported from one place to another, and only a few qualified individuals are supposed to have access to the component, or the component is only to be delivered to a particular location or process, it is important to have a system for ensuring that only the proper individuals are allowed to access the component. It may also be important to record the time at which the component is delivered to its destination, where it is currently located, and similar pertinent information.

Although these problems may appear to be particular to certain industries, the common theme between them all is that there is a need for tracking and permitting access to certain objects, recording relevant information, and doing so with minimum expense, time, and effort.

The present invention is intended to solve these and other problems.

SUMMARY OF THE INVENTION

The present invention provides a system and method for verifying information and activating a response function when two or more pieces of information correspond to each other. Such a system is comprised of an information device and an identification device. The information device has certain identification information stored therein. Additionally, the information device may be adapted to store and be capable of receiving various other information from various sources.

The identification device has an additional set of identification information stored therein or thereon. The information device is capable of receiving or otherwise obtaining the identification information stored in or on the identification device. The information device compares the identification device and information device identification information. If the two sets of identification information correspond, then the information device activates a response function by providing a response signal.

Alternatively, the information device may act as a relay, communicating the identification information from the identification device and other identification information stored in the information device, such as prescription information, via RF communication or some other conventional method, to a remote or local computer comparison system. At the remote or local computer comparison system, the identification information from the identification device and other information are analyzed to determine if the information corresponds, e.g., the information corresponds if the prescription defined by the prescription information is appropriate for a patient identified by the identification information. A comparison result signal is communicated back to the information device indicating whether or not the two sets of information correspond. The information device may then activate a response function by providing a response signal in response to the comparison result signal received from the remote or local computer comparison system.

The response function may comprise an indicator, a locking mechanism, or both. In the case of an indicator, when the two sets of identification information correspond to each other, the information device activates the indicator. The indicator may provide a visual and/or audible signal, informing the user that the two pieces of identification information correspond to each other, thereby verifying the information.

In the case of a locking mechanism, the locking mechanism may control access to another object, such as a container. When the two sets of identification information correspond to each other, the information device communicates with the locking mechanism to unlock the container. This system can be applied in a modified form in the case where there are two or more compartments located inside the container. In such a case, there may be more than two pieces of identification information that are compared to each other. If the identification information corresponds to only one portion of the information in the information device, then fewer than all of the compartments of the container will be unlocked or locked.

An information device in accordance with the present invention may be adapted to receive updated information, via wireless or non-wireless communications, from a remote location, relating to a required change in the contents of a container to which the information device is attached. For example, a container may hold items identified by an information device in accordance with the present invention attached thereto. Prior to comparing the identification information of the information device with the identification information of an identification device, a change, e.g., in the intended use of the items in the container, may be communicated to the information device. An audible or visual indication or message may be provided by the information device when the changed information is received by the information device, or at the time a comparison of identification information is performed, indicating, e.g., that additional items not in the container need to be obtained or that some or all of the contents of the container are no longer to be used.

The present invention is application in many situations and industries. In particular, and for example, the present invention may be employed in a medical setting wherein a system for placing unit doses of medication into a portable container labeled with textual and electronic information is provided. The electronic information or electronic labeling is recorded on an information device. The information device is used in conjunction with other electronic devices to record when the doses of medication are given to a patient, the patient who received the medication, and the healthcare worker, such as a nurse, who administered the medication. The information device can include a sensor for sensing when the container is opened, a date and time clock for determining the time the medication is administered, and a locking mechanism. The locking mechanism locks the medication in the container until an appropriate time has been reached and the appropriate patient has been identified. The electronic labeling can include information regarding the intended patient, the names and quantities of each medication in the container, the time the medication is intended to be given, the physician who ordered the medication, the healthcare worker who dispenses the medication, and other pertinent information.

The information device may be separate from the portable container, and therefore not in contact with the medication, or it can be in integral part of the portable container. The information device includes a computer processor, a memory element, a power source, and a communication device for transmitting and receiving electronic information to and from other electronic devices. The information device can also include a display, such as an LCD.

The information device may be used in conjunction with an automated dispensing system that automatically dispenses desired medications into the portable container, or an automated dispensing system where a healthcare worker manually dispenses medication into the portable container. When medication is dispensed by an automated dispensing machine, the healthcare worker must properly identify themselves. This can be accomplished by the entry of a password unique to the healthcare worker. The healthcare worker then identifies the patient to whom medication is to be given. This may be by selection from a list of patients to whom the healthcare worker has been assigned. The healthcare worker may not select an inappropriate patient or one not in this area of the hospital. If the patient has been transferred outside of the area where the dispenser is located, the dispensing system can alert the nurse to this fact and can prevent any medication from being dispensed. The correct location of the patient may be determined via an information exchange with other computer systems in the hospital, e.g. Admit, Transfer, Discharge System (ADT) using a computer network, or this data can be maintained within the dispenser itself and updated manually.

Having selected a patient, the healthcare worker is presented with a list of medications that have been prescribed for the patient. Medication that can be given at this time, determined by the prescription regimen and the times of previous doses being consumed by the patient, may be distinctly displayed for selection. After selecting one or more medications and the quantity to give, the system dispenses each medication.

As each medication is dispensed, they are placed in the portable container. When all the desired medications have been dispensed, the container is closed, and a textual label may be written on the container with information to identify the patient, the medication, its quantity, when the medication is to be given, and other data as appropriate. The same information is also written electronically to an information device. After being written, the data is verified and attached to the container. The information device includes the medication information described above. Finally, the information device is attached to or otherwise associated with the portable container and presented to the healthcare worker. The information device can be attached to the container so that it locks the medication in the container until an appropriate clearance is granted, or the device can be constructed so that it only detects the opening of the container and communicates any necessary warning to the healthcare worker.

The medication may also be manually dispensed at a workstation from bulk containers into the portable container. The workstation includes a computer and input terminal to enter data, such as medication information regarding the medication placed in the portable container. The healthcare worker then uses the workstation to transmit or write the medication information to the information device. Alternately, the healthcare worker may use a computer workstation to determine the medications due to be given to the patient. By selecting the medication due to be given, the healthcare worker can cause the workstation to automatically prepare medication information for transfer to the information device.

The medication container may be of a single use variety, in which case only the information device is returned to the dispensing system for reuse. When the information device is returned to the dispensing system or presented to a computer workstation, the information device is read to assist in data recording and examined for any errors or operational problems. When the device is read, a variety of data may be retrieved from the information device besides that previously written to it regarding the medication information. This data may include the date and time the container was opened, information confirming that patient identification verification was used to confirm that the medication was given to the correct patient, and the healthcare worker identification of the person who gave the medication to the patient.

The medication information and other data is transmitted to the dispensing machine or the workstation in a format that can automatically be sent to the correct database for the patients records and formatted appropriately for the database system. An example of this is the creation of a Universal Record Locator (URL) address compatible with a hospital Intranet network. The address may be in a format not normally known to the dispensing system. Thus, the dispensing system can be used in several different hospitals without having to be significantly modified to accommodate differing address schemes. A medication report can also be formatted in a manner compatible with the Hypertext Markup Language (HTML), which will help preserve the independence of the dispensing system from the specific software requirements of the nurse reporting and charting system, which may vary from hospital to hospital.

In the case of any errors or operational problems being detected (e.g., inability to read the information stored in the information device, or battery beyond its expected service life), the device will be removed from service and stored in an area for retrieval by a service technician. A failure or service request message can be presented to the healthcare worker or sent by computer network to the pharmacy or hospital engineering department.

The information device will be compatible with a patient identification verification system. Such a system can transmit some or all of the patient identification information to the information device. This may be done by a communication between a patient information device, with a compatible communication device, attached to or associated with the patient and the information device. It may also be done by communication from a patient information device to a computer processor associated with a healthcare worker with a compatible communication device. The patient identification information is then communicated to the information device. The healthcare worker computer processor may be a workstation the worker has logged into, a portable computer device (e.g., personal digital assistant—PDA), or a healthcare worker information device such as an electronic badge that is worn. The healthcare worker computer processor is in some manner known to be temporarily or permanently associated with the patient, for example, by having recently read the patient information device. In this case, the medication information held in the information device can be transmitted to the healthcare worker computer processor and in turn can later be transferred to the dispenser or a computer workstation for prompt and automatic data recording or for transmission to database computer system as described above.

The information device may also be adapted to receive updated medication orders. For example, the information device may receive communications from, e.g., the hospital computer system indicating that there has been a change in the medication order contained in the container to which the information device is attached (e.g., medication is cancelled and/or added to a prescription). This information relating to a required change in the contents of the container to which the information device is attached may be presented to a user as a display or alarm, which may be presented by the information device when the container is opened or an identification verification is attempted.

A portable information device in accordance with the present invention may also be employed as part of an infusion pump control system. Infusion pump control information (e.g., prescribed flow rates and durations) may be stored in the information device. The information device may then be attached to the appropriate IV bag, which is conveyed to the infusion pump. At the infusion pump, the control information is communicated to the infusion pump controller from the information device. This system may be employed in combination with a patient verification system to ensure that the correct patient is provided with the correct IV prescription.

Other aspects and advantages of the invention will become apparent upon making reference to the specification, claims and drawings.

BRIEF DESCRIPTION OF THE DRAWINGS

FIG. 17 is a listing of the memory contents of the information device.

FIG. 18 is a listing of patient medication information.

FIG. 19 is a listing of dispensed medication information.

FIG. 20 is a listing of the memory contents of the patient information device.

FIG. 21 is a listing of the memory contents of the healthcare worker identification device.

FIG. 22 is a listing of the memory contents of a patient room workstation or computer peripheral device.

FIG. 23 is a listing of final medication transaction report.

FIG. 24 is a medication report for transmission in an HTML format.

FIG. 25 is a universal resource locator data storage address.

FIG. 26 is a medication report for transmission in an HTML format.

FIG. 27 is a universal resource locator data storage address.

FIG. 28 is a medication report as displayed on a computer monitor.

DESCRIPTION OF THE PREFERRED EMBODIMENTS

Figure 14:
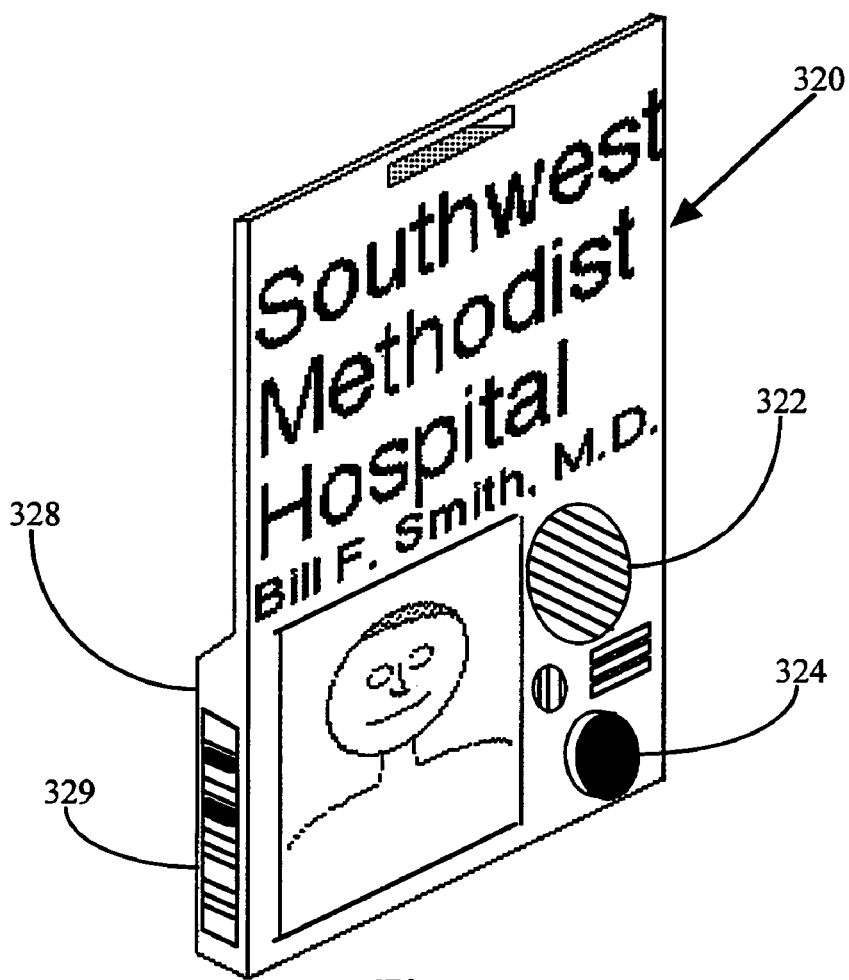
FIG. 14 is a perspective view of a healthcare worker identification device.

A verification apparatus in accordance with the present invention comprises an information device 10 and an identification device 300, 320. The identification device 300, 320 includes identification device identification information 621, 681. The types of identification device identification information 621, 681 that can be included in the identification device 300, 320 are almost limitless. In a preferred embodiment of the invention, identification device identification information 621, 681 may include the name of an individual worker, the worker's position, job description, qualifications, certification, and duties, and what tasks the worker is authorized to perform. The identification device 320 can be as small as a credit card or an ID badge, as shown in FIG. 14. Identification device identification information 621, 681 can be stored in memory in the identification device or on the identification device 300, 320 via either a bar code, a magnetic strip, or other similar means.

The information device 10 is preferably portable and is also capable of having identification information stored therein. Information device identification information (exemplified as selected patient identification information 520) can also cover a variety of matters. The information device 10 can include information about the contents of an attached container 100, the day's date and time, the location of the information device 10, and individuals who are entitled to have access to the contents of the attached container 100.

The information device 10 also includes means for reading or otherwise obtaining the identification device identification information 621, 681. In an embodiment where the identification device identification information 621, 681 is stored as a bar code 319, 329, the means for reading this information is comprised of a scanner. When the identification device identification information 621, 681 is stored on a magnetic strip, the means for reading this information can be in the form of a magnetic strip reader.

Figure 10:
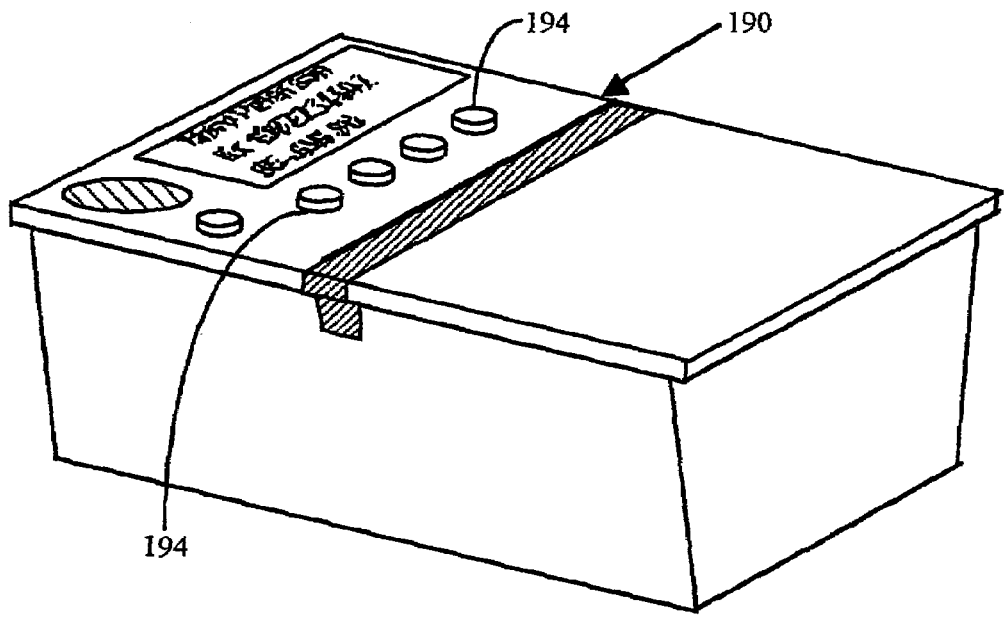
FIG. 10 is a perspective view of an integral portable container and information device with the information device built into its cover.

In a preferred embodiment of the invention, the verification apparatus also comprises a container 100. The present invention may be employed in combination with any type of container. (Container 100 as illustrated is only exemplary of the types of containers which may be employed. Container 190, shown in FIG. 10, is another example.) This container 100 may store items of various sizes ranging from individual pieces of medication to large personal belongings, items or parts of manufacture, etc. Although the container 100 is preferably portable, it can be integrally connected to the information device and can also remain in a fixed position depending upon the intended use. In a more preferred embodiment of the invention, the container 100 includes a latching mechanism for opening and closing a door of the container 100. The container 100 may also include a sensor 86 for providing an indication when the container is opened or is attempted to be opened.

The operation of a verification apparatus in accordance with the present invention is as follows: the identification device 300, 320 is presented to the information device 10. The information device 10 then obtains the identification device identification information 621, 681 from the identification device 300, 320. The information device 10 then proceeds to compare the identification device identification information to the information device identification information 520 stored therein. In the event that the identification device identification information 621, 681 and the information device identification information 520 correspond to each other, then the information device 10 activates a response function by providing a response signal.

Alternatively, the information device 10 may relay the identification information obtained from the identification device 300, 320, along with other information device identification information, such as prescribed medication information 580, to a remote or local (attached) computer comparison system. This communication may be performed in a conventional manner using RF communication, employing an RF transmitter/receiver in the information device 10, or by any other conventional wired or wireless communication method. A determination is made if the identification device identification information corresponds with the information device information by the remote or local computer comparison system. For example, where the communicated information device information is prescription information 580 and the identification information is patient identification information obtained from a patient identification device 300, a determination may be made by the comparison system whether or not the prescription information and identification information correspond. Correspondence may be found by the comparison system if the prescription is appropriate for the identified individual. (In this case, the comparison system may be part of a medication dispensing system.) The computer comparison system may provide an identification information comparison result signal back to the information device 10, over the same or a different communication channel, indicating the result of the determination. The information device 10, in turn, may activate a response function by providing the response signal in response to the received comparison result signal.

In a preferred embodiment of the invention, the response function is in the form of unlocking a latching mechanism on the container 100. This action allows the user to access the contents of the container 100. In an alternate embodiment of the invention, the response function is in the form of either an audible or visual indicator. For example, when the two pieces of information correspond to each other, then the indicator could produce an audible noise informing the user that the identification device identification information has been accepted. The information device 10 may also activate a response function when the two pieces of information do not correspond to each other, or if the two pieces of information do not correspond to each other and a sensor indicates that the container 100 to which the information device is attached was opened or was attempted to be opened nevertheless. In such a case, the response function could be in the form of audio or visual alert signal. Also, the opening of, or attempt to open, the container 100 when the two pieces of identification information do not match may be noted in memory 62 of the information device for later examination or communication to a remote computer system. Whenever an indicator is used, it may indicate that the information does or does not correspond. The response function is preferably integrally connected to the information device 10.

The verification apparatus may also include several peripheral items. For example, the information device 10 may include data entry means such as a computer keyboard for modifying or inputting new information device identification information (e.g., selected patient information 520) to be stored in the information device 10. The verification apparatus may also include output means such as an LCD display 34. This display 34 may be used for either sending alert messages to the user or for displaying pertinent information device identification information or identification device identification information. Additionally, the verification apparatus may include a printer or other means for transcribing information located on either the information device or the identification device.

Figure 32:
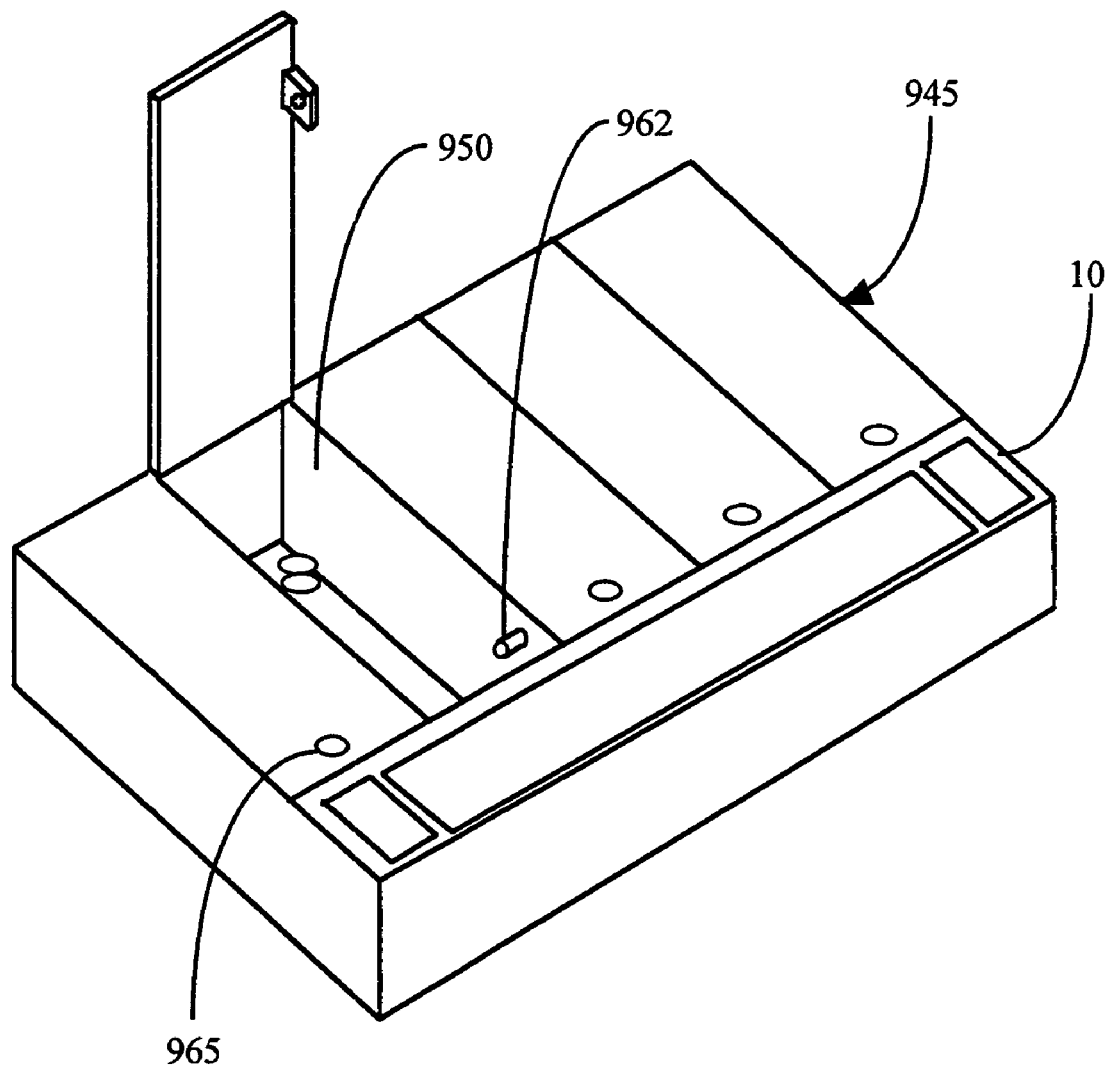
FIG. 32 shows a container with multiple compartments according to one embodiment of the invention.

In an alternate embodiment of the invention, a container 945 may be modified to include multiple compartments 950. As shown in FIG. 32, each compartment 950 includes separate latching mechanisms 962 for opening and closing individual compartments 950. The information device 10, which may be integrally formed with the container 945, may include information device identification information (e.g., selected patient information 520) for each compartment 950 of the container 100. (See FIG. 17.) When identification device identification information 621, 681 is presented to the information device 10, only those compartments 950 for which the information device identification information 520 corresponds to the identification device identification information 621, 681 would be capable of being opened. Additionally, or alternatively, an indicator, such as an LED 965 or an audible tone, may be provided when there is correspondence of selected identification information for selected compartments 950 of the container 945. This could be very important in a hospital setting where the same verification apparatus could be utilized to control prescription drugs for several different patients held in the same container. By having multiple compartments 950 with their own associated information device identification information 520, one apparatus could be used while still ensuring that the wrong medication is not given to the wrong person. Individual compartments 950 may also only be opened, and/or an indication provided, when an appropriate time for opening the compartment (e.g., to dispense medicine) is reached. Thus, different medications may be provided to a patient at appropriate times during a day.

While this invention is susceptible of embodiment in many different forms, the drawings show and the following specification describes in detail, and for example, a preferred embodiment of the invention. It should be understood that the drawings and specification are to be considered an exemplification of the principles of the invention. They are not intended to limit the broad aspects of the invention to the embodiment illustrated. In particular, although the present invention is described in detail with reference to the exemplary application of dispensing medication in a hospital setting, the present invention is applicable in many other situations and settings, including commercial and industrial applications. Thus, it should be understood that, throughout the following description, reference to a "patient" can be considered an exemplary reference to a larger class of generic "objects" to be identified, "medication" can be considered an exemplary reference to generic "materials" or "goods" to be contained in a container, a "healthcare worker" is an exemplary reference to a generic worker or other authorized person, and a medication "prescription" is an exemplary reference to a generic type of process order.

Information Device and Portable Container

Figure 1:
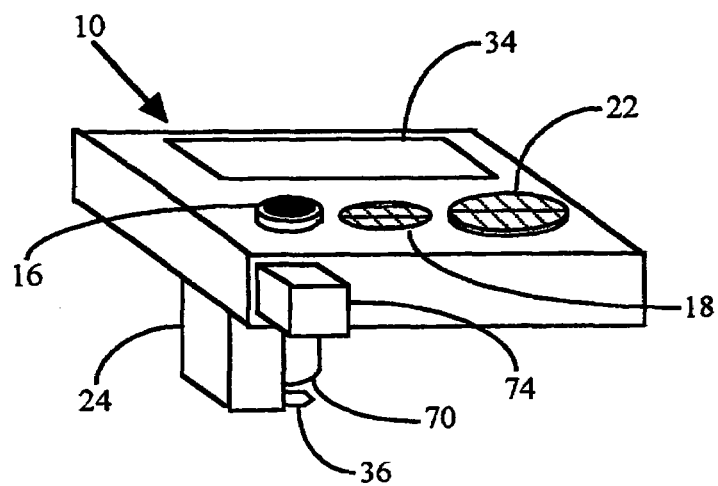
FIG. 1 is a perspective view of an information device having a latch for locking a portable container into a closed position.
Figure 2:
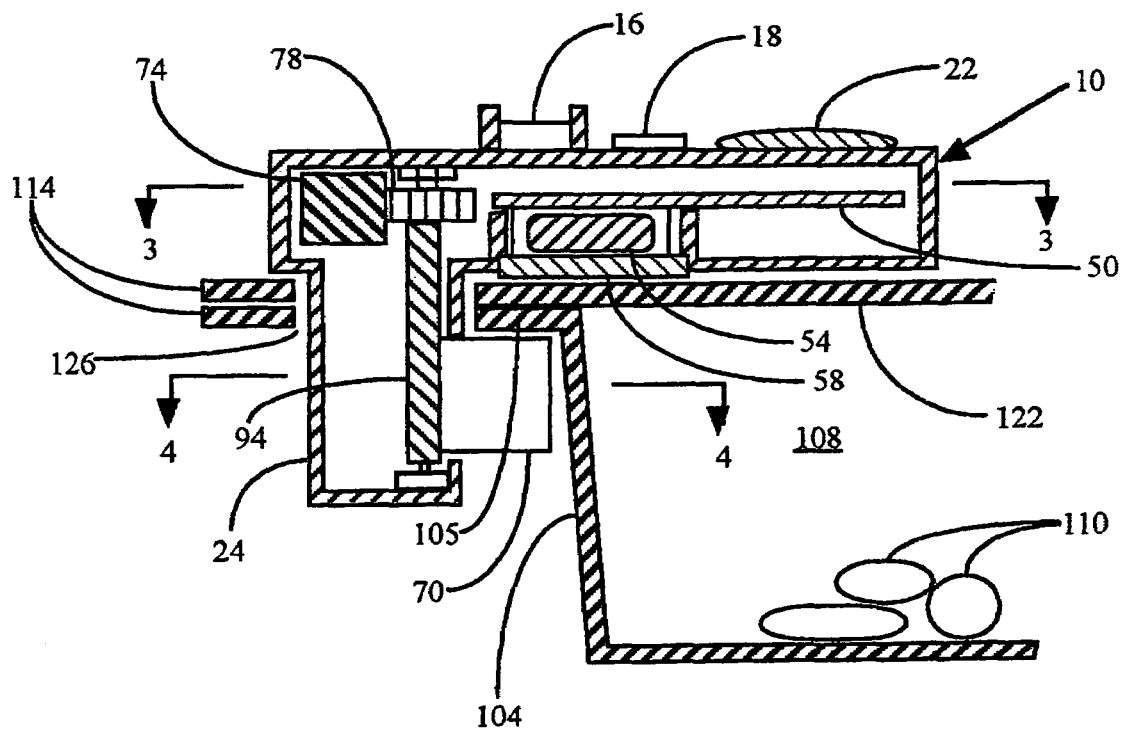
FIG. 2 is a sectional view of the information device attached to the container, with the latch of the information device locking the container into its closed position.

An information device 10 is shown in FIGS. 1–4. The information device 10 includes activation button 16, audible alert device 18, infrared receiver and transmitter or transceiver device 22, alignment projection 24 with securing latch 70, and latch release button 74. Securing latch 70 is movable between a locked position 71 and an unlocked position 72. The information device 10 also includes an optional display device 34 or visual display 34 which may be an LCD device, and optional sensing switch 36. While the infrared transceiver 22 is shown and infrared communications described, it should be understood that many other methods of communication can be used, such as radio frequency communication, magnetic induction, direct electrical contact, ultrasound, 802.11 protocols, cellular communications, and the reading of bar codes or magnetic strips. Thus, the information device 10 may include, additionally, or alternatively, a conventional bar code or magnetic strip reader. As best shown in FIG. 2, the internal components of the information device 10 include a processor 50, power source or battery 54, battery cover 58, and latch movement gear 78. It should be understood that the power source 54 may be a solar energy device, or it may be an external device providing energy by magnetic coupling or radio frequency transmission.

Figure 5:
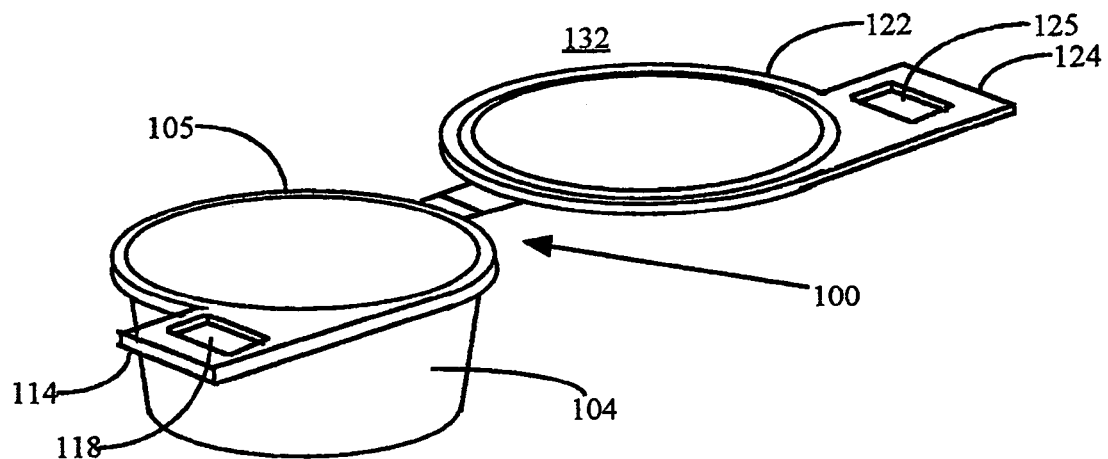
FIG. 5 is a perspective view of a portable medication container in an open position.
Figure 6:
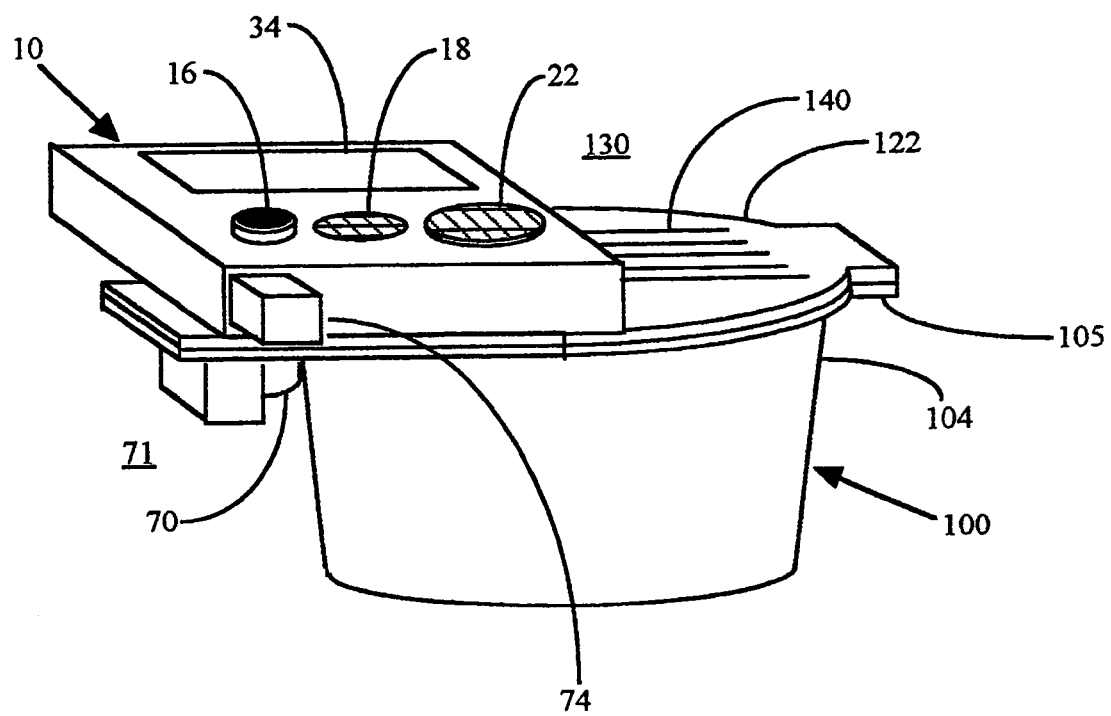
FIG. 6 is a perspective view of the portable medication container with the information device attached thereto and locking the container into its closed position.

A portable container 100 is shown in FIGS. 2, 5, and 6. The portable container 100 includes base 104 forming compartment 108. The container 100, and thus the compartment 108, may be sized and shaped to hold any desired item or items of interest. For exemplary purposes, the compartment 108 illustrated in the figures is for holding a prescribed dose of medication 110. The base 104 has a rim 105 that forms an open top. One side of the rim 105 has an integral, projecting tab 114 with a hole 118 formed through its middle portion. The container 100 includes container lid 122 that is hingably attached to the other side of the rim 105. Lid 122 also has an integral, projecting tab 124 with a hole 125 formed through its middle portion. As shown in FIGS. 2 and 6, the hole 118 in the tab of the rim 114 is adapted to align with the hole 125 in the tab of the lid 124 when the lid is in a closed position 130. The holes 118 and 125 combine to form an opening 126 when in this closed position 130. The information device 10 is adapted to attach to the portable container 100 when the lid is in its closed position 130. The alignment projection 24 of the information device 10 passes through the opening 126 and combines with the forward extension of the securing latch 70 to prevent base 104 and lid 122 from separating and moving to an open position 132.

Figure 3A:
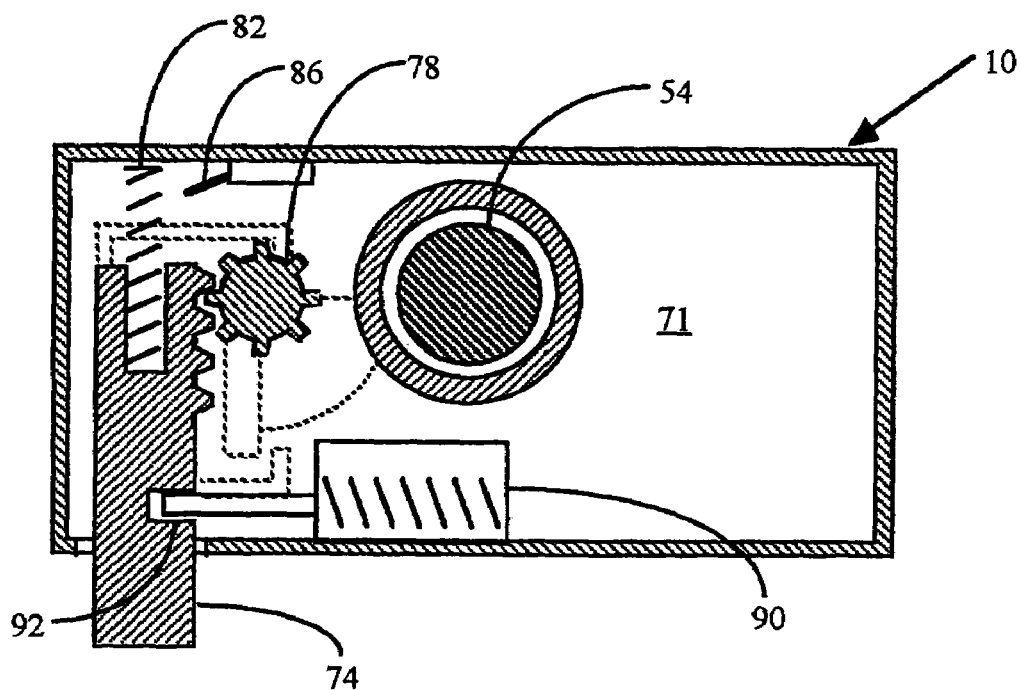
FIG. 3A is a sectional view of FIG. 2 taken along line 3—3 showing the locking mechanism of the information device with its latch in a locked position.
Figure 4A:
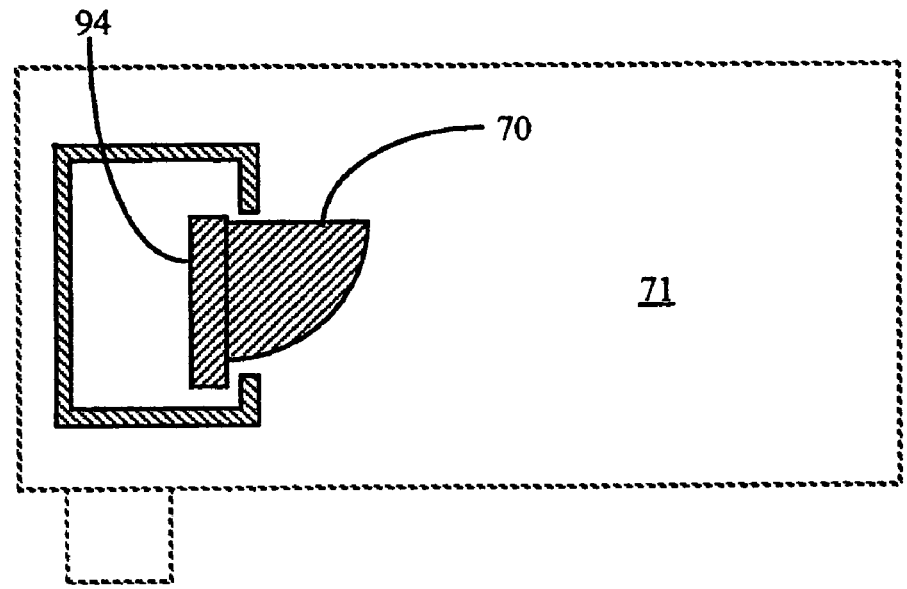
FIG. 4A is a sectional view of FIG. 2 taken along line 4—4 showing the locking mechanism of the information device with its latch in its locked position.

In FIGS. 3A and 4A, the securing latch 70 is shown in its locked position 71. Latch release spring 82 biases latch release button 74 into its extended position. An electric switch 86 is used to sense the motion of the button 74. An optional latch release solenoid 90 and the geared rack engage latch movement gear 78. A movable rod of latch release solenoid 90 is biased to extend into slot 92 to prevent the latch release button 74 from moving. The latch 70 includes a backing door 94 to keep foreign material out of the information device 10.

Figure 3B:
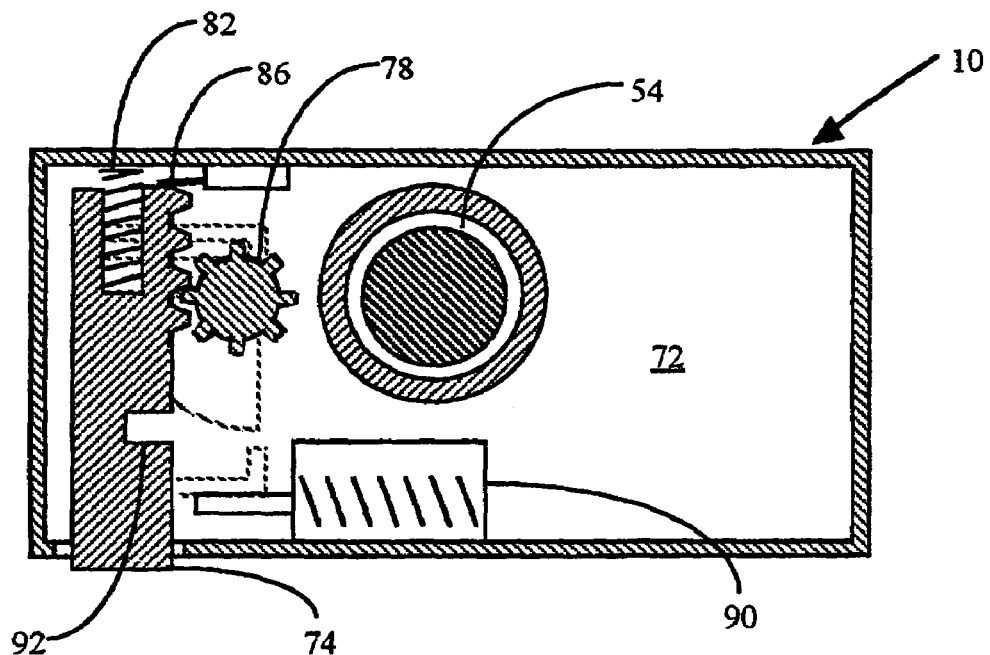
FIG. 3B is a sectional view of FIG. 2 taken along line 3—3 showing the locking mechanism of the information device with its latch in an unlocked position.
Figure 4B:
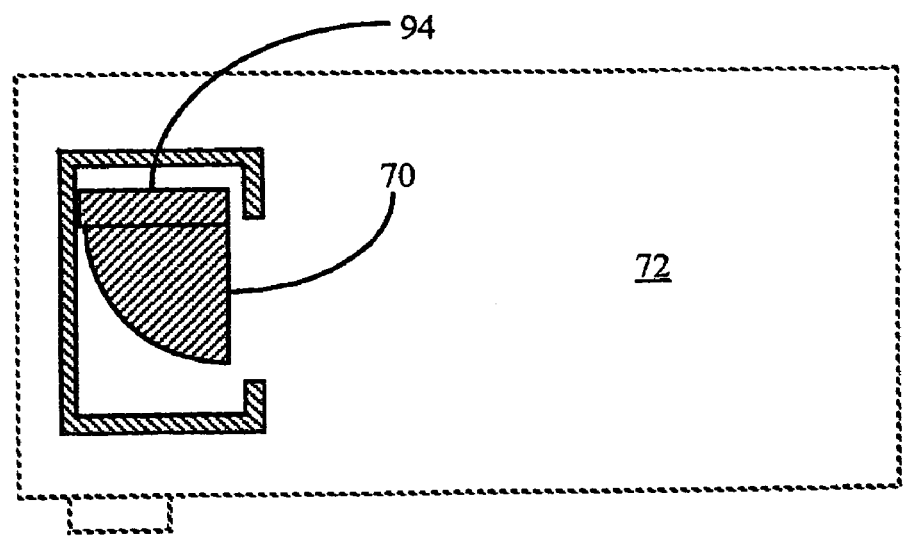
FIG. 4B is a sectional view of FIG. 2 taken along line 4—4 showing the locking mechanism of the information device with its latch in its unlocked position.

FIGS. 3B and 4B show the securing latch 70 is in its unlocked position 72. Securing latch 70 moves into unlocked position 72 when processor 50 receives appropriate instructions via transceiver device 22 to retract latch release solenoid 90. With the movement rod of the solenoid 90 retracted, latch release button 74 can be depressed to cause latch movement gear 78 to rotate and allow securing latch 70 to swing away from the locked position 71. Electric switch 86 is closed which indicates the button 74 was pressed. When the latch release button 74 is released, spring 82 will again bias the latch release button into its extended position. When the solenoid 90 is deactivated its movement rod will again extend into slot 92, securing latch 70 into its locked position 71.

FIG. 5 shows the portable container 100 in its open position 132. Container 100 may be a disposable container intended for a single use to prevent medication cross contamination. The lid 122 includes a paper label 140 for printing textual labeling information as shown in FIG. 6. Alignment projection 24 can pass through the opening 126 so that the information device 10 can be removed, when securing latch 70 is retracted into its unlocked position 72, but not when the securing latch is extended into its locked position 71. FIG. 6 shows information device 10 secured to container 100 in its closed position 130. The latch 70 is in its locked position so that the container 100 cannot be opened. The doses of medication are locked inside the closed container 100. The display device 34 is provided to display a desired portion of the information contained in memory contents 500 of the information device 10. See FIG. 17, as discussed below.

Figure 7:
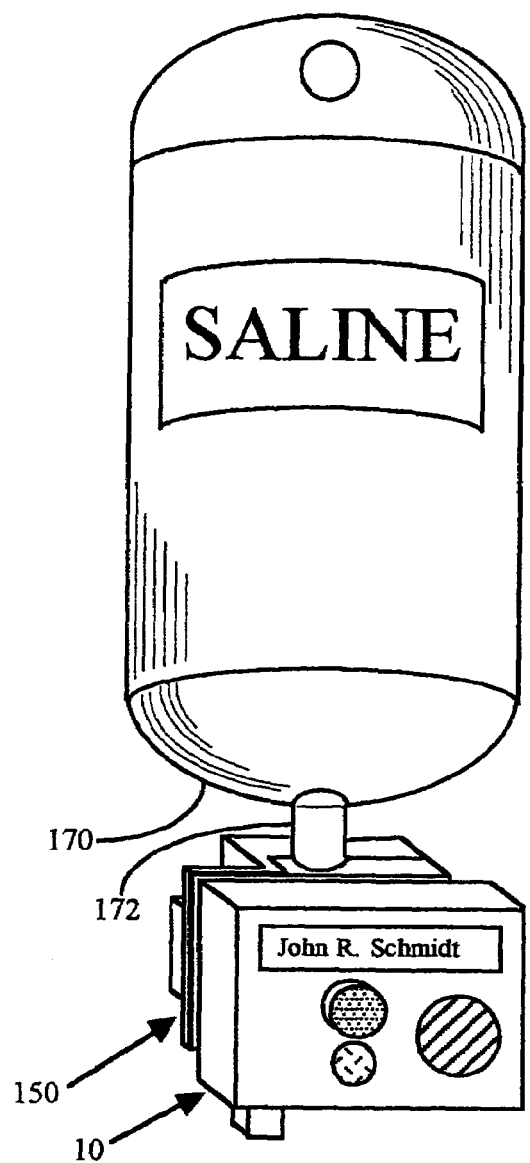
FIG. 7 is a perspective view of an information device attached to a securing device that is secured to a fluid bag for holding IV or blood solutions, the securing device being in a locked position to prevent access to the IV solution via a nipple or tip of the fluid bag.
Figure 8:
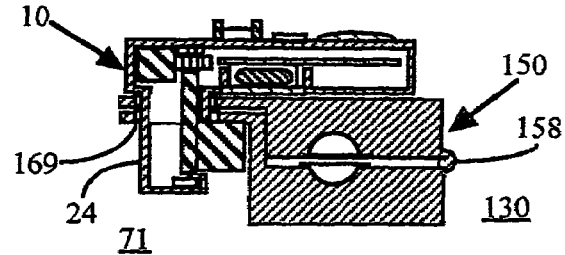
FIG. 8 is an elevated sectional view of an information device and securing device in its locked position.
Figure 9:
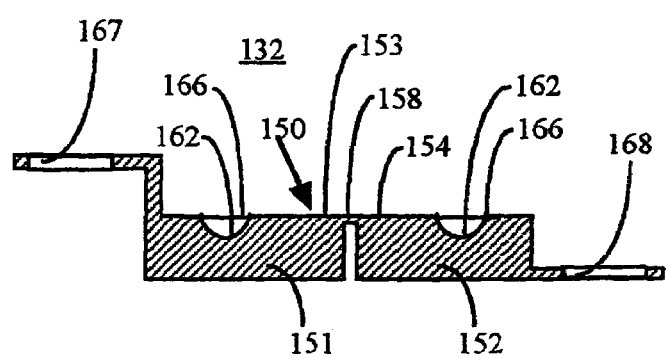
FIG. 9 is an elevated sectional view of a securing device in an open position to allow access to the nipple or tip of the fluid bag.

FIGS. 7 to 9 show the information device 10 used in conjunction with a fluid bag securing device 150 and a fluid bag 170. The information device 10 assists in the electronic labeling of fluid bag 170 containing IV solutions or blood. Securing device 150 is an integral piece of plastic with first and second clamping portions 151 and 152 with upper surfaces 153 and 154. The clamping portions are joined by a living hinge 158 located proximal the upper surfaces. Each clamping portion has a recess 162 and a pressure ridge 166. As shown in FIG. 8, the hinge 158 enables the clamping portions to fold so the recesses 162 and pressure ridges 166 can tightly surround an extended tip 172 of fluid bag 170 preventing flow or normal use of the fluid bag 170. When securing device 150 is folded, holes 167 and 168 form opening 169 allowing alignment projection 24 to pass through when securing latch 70 is retracted, but not when it is extended. FIGS. 7 and 8 show the securing device 150 in closed position 130 surrounding and securing fluid bag tip 172 with the information device 10 attached in locked position 71.

FIG. 10 shows an integral portable container and information device 190 which may be used for IV bags 170, syringes, body tissues, body organs, or other larger objects such as personal items or items used in, e.g., manufacturing, industrial or other processes. The information device 10 is an integral part of the covering lid. Optional data entry buttons 194 are provided to enter data or modify information about medication given to a patient or otherwise concerning the contents of the container 190. It should be understood that data entry buttons 194 could also be provided on information device 10.

Figure 11:
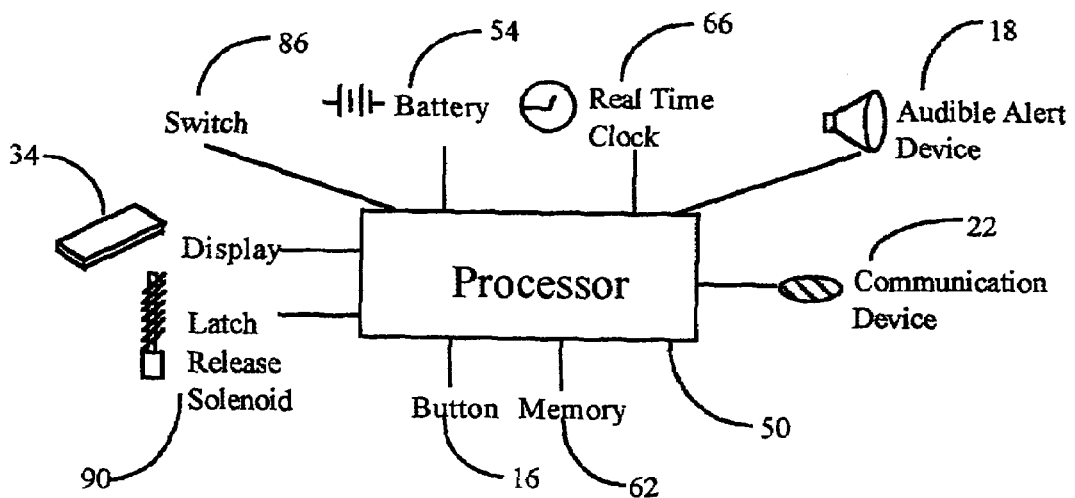
FIG. 11 is a schematic drawing of the electronic circuitry for the information device.

FIG. 11 is a schematic circuit diagram for information device 10 or the information device portion of integral container 190. The information device 10 includes computer processor 50, memory element 62, and real time clock 66 as well as controls to interact with activation button 16, latch release solenoid 90, optional display device 34, battery 54, audible alert device 18, and communication device 22 (which may be an infrared, radio frequency, etc. communication device, or a bar code or magnetic strip reader, etc.).

FIG. 17 shows a list of memory contents 500 maintained in the memory element 62 of the information device 10. The memory contents 500 includes information specific to the information device 10, such as information device data elements 504 which contain a serial number 505, end of battery life data 506, and communication encryption codes 507. As discussed elsewhere herein, the information device 10 may be used in combination with a container 945 having a plurality of individual compartments 950. In such case, the memory contents 500 may also include information on the number of compartments 508.

The memory contents 500 includes information received from other electronic devices, such as the automated or manual dispensing systems 200 or 280 as discussed below. Information received from dispensing systems 200 or 280 can include selected predetermined patient information 520, selected prescribed medication dose information 540, predetermined healthcare worker information 560, dispensed medication information 580, medication information 581 and medication report components 600. Memory contents 500 can further include specific patient information 621 received from a patient identification device 300, a healthcare worker identification device 320, or a patient room information workstation 350 or computer peripheral device 355. Memory contents 500 can include administering healthcare worker information 681 received from the healthcare worker identification device 320.

Memory contents 500 can include consumption information 640 generated during use. Consumption information 640 can include consumption time information (e.g., consumption date and time information) 642 regarding when the portable container was opened 642, offered medication amount information 643 regarding the amount of medication offered to a specific patient 360, and consumed medication amount information 644 regarding the actual amount of medication consumed by the specific patient 360. Memory contents 500 can include a final medication transaction report 660. It should be understood that the memory contents 500 may include additional elements or fewer than shown in FIG. 17. For use with a container 945 having a plurality of individual compartments 950, selected memory contents 500 may include information elements unique to selected ones of the compartments. Each of these sources of information and the use of the various information elements 500 can vary based on the intended use of information device 10 such as in a patient verification system, healthcare worker authorization system, medication tracking system, etc. as more fully described below, or in another medical or non-medical application or setting.

Automated Dispensing System

Figure 12:
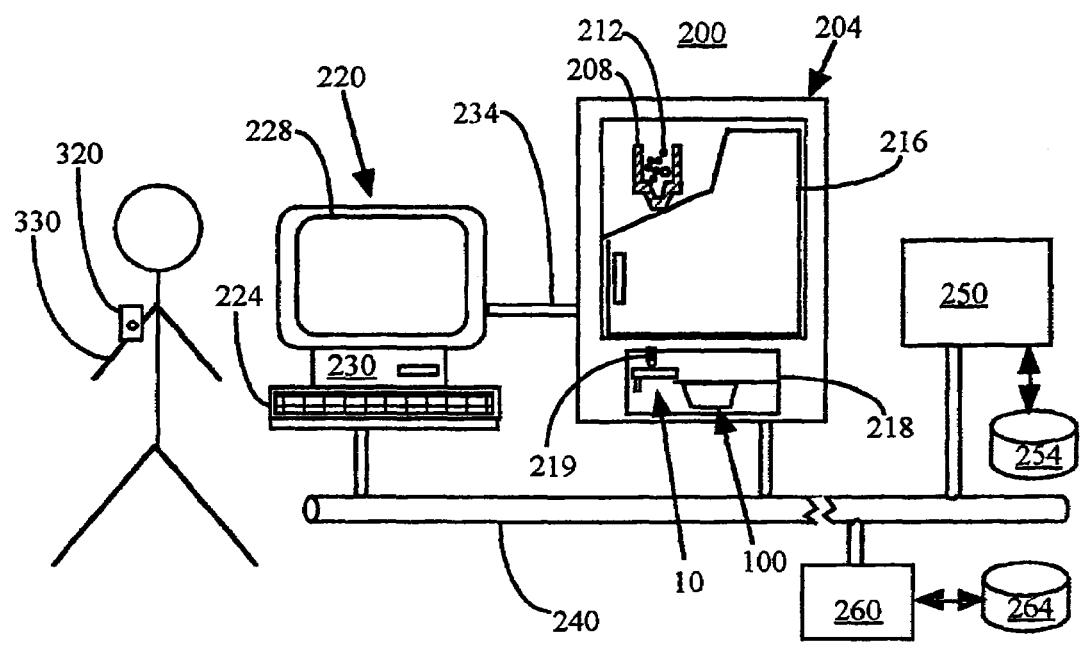
FIG. 12 is a plan view of a healthcare worker using an automated dispensing system that includes a dispensing machine and a medication dispensing workstation, both connected via a hospital network to a pharmacy database and a hospital database.

FIG. 12 shows the automated dispensing system 200 including an automated dispensing machine or unit dose dispenser 204 containing a plurality of bulk medication containers 208 stored inside the dispenser. Each bulk container 208 contains a specific type of medication 212. An access door 216 to the bulk containers 208 is kept locked. Access to the containers 208 is limited to authorized personnel in charge of maintaining the inventory of medication 212 in the dispenser 204, such as the hospital pharmacist. The dispensing machine 204 also contains an access port 218 through which the filled and sealed portable containers 100 are dispensed. A transceiver device 219 is provided for communicating information to the information device 10. Dispenser 204 is used in conjunction with a dispensing workstation 220.

The dispensing workstation 220 includes an input terminal 224 such as a keyboard or a pointer device, and a monitor 228 for communicating with the dispensing machine 204. The workstation 220 also includes a computer processor 230 and program software for controlling the operation of the dispenser 204 and the flow of information and instructions to and from the dispenser. The dispenser 204 or workstation 220 can communicate by a direct communication line 234 or via a hospital network 240. However, it should be understood that the computer processor 230 or an alternate computer processor could be located directly inside the dispenser 204 or included as a part of a hospital network 240.

The hospital network 240 can include its own internal database or can be connected to a pharmacy system 250 with pharmacy database 254 or a hospital information system 260 with a hospital database 264. The internal database or the workstation, or the separate databases 254 and 264 of the pharmacy and hospital systems 250 and 260, contains information pertaining to a plurality of physician orders such as prescription regimens or prescribed medication dose information 540 for administering medication 212 to a plurality of predetermined patients listed in at least one of the databases. The databases include predetermined patient information 520 and corresponding prescribed medication dose information 540 for each patient in the database. The computer processor 230 of the workstation 220 communicates with and obtains information from and relays information to its internal database, pharmacy database 254 or hospital database 264.

A healthcare worker 330 uses the automated dispensing system 200 to obtain prescribed doses of medication 110 for a specific patient 360 under his or her care. Before the dispensing machine 204 dispenses medication 110, the workstation 220 requests the healthcare worker 330 to select one of the predetermined patients in the database. The selected predetermined patient or selected patient should correspond to the specific patient 360 under his or her care. The healthcare worker 330 dispenses the prescribed dose or doses of medication by entering some form of selected patient information 520 that corresponds to the selected patient listed in the database. Alternatively, the healthcare worker 330 can select the name of the desired predetermined patient from a list of predetermined patients in the workstations internal database or by using the hospital information system 260 to locate the desired predetermined patient from the hospital information database 264. The list of predetermined patients to choose from may be limited to those who have been assigned to healthcare worker 330. Having identified the selected patient from the database 262 that corresponds to the specific patient 360 under his or her care, dispensing workstation 220 locates patient medication information 700 (see FIG. 18) for the selected patient in the workstations internal database or by using pharmacy system 250 to locate the information in pharmacy database 254.

Patient medication information 700 contained in the workstation database or associated databases 254 or 264 includes predetermined patient information 520 and corresponding prescribed medication dose information 540 for each predetermined patient. The physician prescription orders determine what prescribed medications correspond to which patient. The database also includes predetermined healthcare worker information 560 that is associated with the prescribed medication dose information. The prescribed medication dose information includes information designating what title or level of authority or clearance an authorized healthcare worker must have to administer the medication to a patient. Predetermined patient information 520 can include patient identification number 521, patient name 522, admitting physician 523, and patient room number 524, and patient blood type 525. The predetermined patient information preferably includes at least patient identification number 521.

Prescribed medication dose information 540 for each prescribed dose of medication 110 can include medication type 541, medication quantity prescribed 542, dosing times 543, and identification of physician prescribing medication 544. Patient medication information 700 can include medication report 720 (see FIG. 24) and universal resource locator 724 (see FIG. 25) which are reformatted by information device 10 as described infra. Predetermined healthcare worker information 560 can include the responsibilities, title, or level of authority of the healthcare worker 561 allowed to give the prescribed medication, healthcare worker identification number(s) 562 allowed to give the prescribed medication, healthcare worker names(s) 563 allowed to give the prescribed medication, and list of patients 564 under care of each healthcare worker. Predetermined healthcare worker information preferably includes the responsibilities, title, or level of authority of the healthcare worker 561.

The computer processor 230 and monitor 228 present prescribed medication dose information 540 for the medications that have been prescribed for the selected patient. The healthcare worker 330 then selects the medication to dispense from this list. Healthcare worker 330 can also enter a medication to be dispensed without the aid of the list or not on the list. In either case, computer processor 230 determines whether the medication is stocked in any of the holding containers 208. If not, an error message will be presented or displayed on the monitor 228. If the medication is available, computer processor 230 causes the dispenser 204 to dispense individual doses of the selected medication 110. As each dose of medication 110 is dispensed, they are placed in the compartment 108 of portable container 100. When all the doses of medication 110 have been dispensed, the lid 122 of the container 100 is closed by dispenser 204 to preventing access to medication.

As medication 212 in the bulk container 208 is dispensed for the selected patient, computer processor 230 creates dispensed medication information 580 for the doses of medication 110 dispensed. Dispensed medication information 580 can include medication information 581, date and time medication dispensed 582, identification of healthcare worker 583 who dispensed medication, and type and quantity actually dispensed 584. Dispensed medication information 580 can also include medication report components 600, medication report 720, and universal resource locator 724 whose use are discussed below.

When all the prescribed doses of medication 110 for the selected patient are dispensed into the portable container 100, selected portions of patient medication information 700 and dispensed medication information 580 are communicated to information device 10 by dispenser 204 using transceiver device 219 via a dispensing signal. This is shown in steps 800, 860, and 910 in FIGS. 29A, 30A, and 31A. The transferred information is stored in the memory element 62 of the information device 10. The use of the selected portions of patient medication information 700 vary based on the intended use of information device 10 such as in a patient verification system, healthcare worker authorization system, medication tracking system, etc., as more fully described below.

Information device 10 may intermittently turn itself off to conserve power when stored in the dispenser during periods of non-use. The dispenser 204 can press activation button 16 to initiate the transfer of data. The data received by the information device 10 can be communicated back to the dispenser 204 as part of a verification process.

Once information device 10 receives the dispensing signal, computer processor 230 sends a message to the information device 10 to retract the latch release solenoid 90. The dispenser 204 automatically presses the latch release button 74 to cause securing latch 70 to swing to its unlocked position 72. This step may also be accomplished manually by healthcare worker prior to inserting the information device 10 into the dispenser 204. Latch release button 74 also makes contact with electric switch 86 which is sensed by processor 50 and causes latch release solenoid 90 to be biased to return to its extended position. Projection 24 of the information device 10 is now aligned with and moved along a path of travel so that the projection passes through the opening 126 formed by the base 104 and closed lid 122. The bottom surface of the information device 10 now rests on the upper surface of the lid 122 of the container 100. Latch release button 74 is then released to allow the spring 82 to force latch release button to move into its extended position 71, so that securing latch 70 rotates to its extended or locked position 71. The upper surface of the latch 70 now abuts the lower surface of the rim 105 of the container 100. Latch release solenoid 90 then enters slot 92, which prevents securing latch 70 from moving out of its locked position 71. The container 100 is now removed from dispenser 204 through access port 218. Access port 218 can be secured to prevent removal of container 100 until information device 10 has been secured and locked to the portable container 100.

When prescribed dose or doses of medication 110 are dispensed into portable container 100, the dosing times 543 or time ranges for when the medication is to be administered can be included with the dispensing signal transferred to information device 10. Dosing times 543 are used by processor 50 in conjunction with real time clock 66 to prevent latch release solenoid 90 from being retracted until the prescribed time or time range is reached. This feature helps prevent the healthcare worker 330 from administering the medication inside the container 100 to the specific patient 360 under his or her care too soon. Processor 50 can also use its audible alert device 18 to issue a reminder tone when the time or time range is reached. This tone is used to indicate to the healthcare worker 330 transporting the medication that it is time to administer doses of medication 110 to the predetermined patient.

Manual Dispensing System

Figure 13:
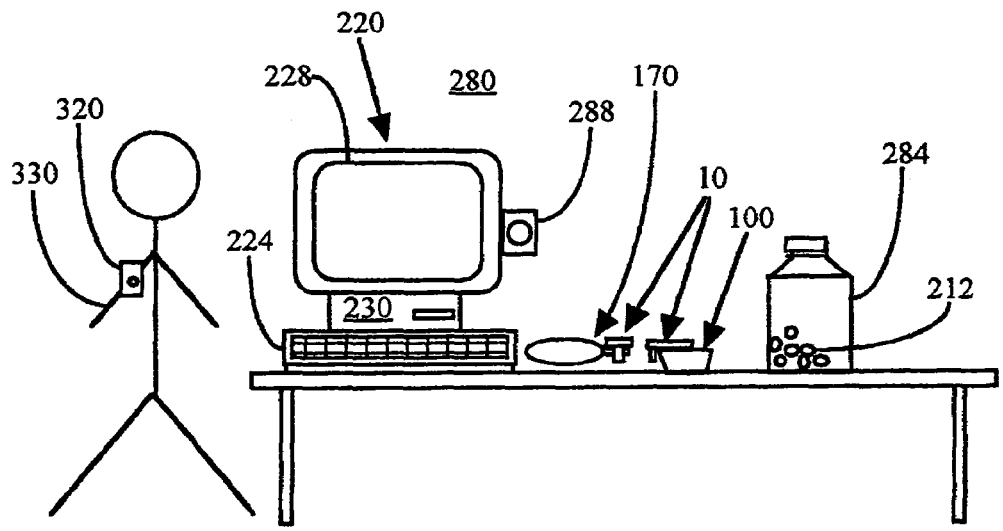
FIG. 13 is a plan view of a healthcare worker using a manual dispensing system with the healthcare worker using the dispensing workstation for manually dispensing medication and labeling medication containers.

FIG. 13 shows the manual dispensing system 280 which includes dispensing workstation 220. Healthcare worker 330 manually locates a bulk medication container 284 holding a quantity of a specific type of medication 212 for dispensing to a specific patient 360 under his or her care. Healthcare worker 330 then removes the prescribed dose or doses of medication 110 from container 284 and places these doses in compartment 108 of portable container 100, and closes lid 122. Healthcare worker 330 then uses workstation 220 to identify the medication and the amount of that medication that has been selected and placed in the container 100 for administering to the predetermined patient. Healthcare worker 330 may also use input terminal 224, to identify the medication selected for administering to the selected patient from patient medication information 700.

When all the prescribed doses of medication 110 for the selected patient are manually dispensed into portable container 100, selected portions of patient medication information 700 and dispensed medication information 580 are communicated to information device 10 via communication port 288 which transmits the initial dispensing signal to the information device 10 for storage in memory element 62. If the patient medication information 700 is not available, portions of selected patient information 520 and predetermined healthcare worker information 560, as entered by healthcare worker 330 using workstation 220, may be sent as part of the dispensing signal. This is shown as steps 800, 860, and 910 in FIGS. 29A, 30A, and 31A.

The healthcare worker 330 manually secures the information device 10 to the container 100. This is done by closing the lid 122 of the container, pressing latch release button 74, inserting the projection 24 of the information device into the opening 126 of the container. The bottom surface of the information device 10 now rests on the upper surface of the lid 122 of the container 100. The healthcare worker then releases latch release button 74 so that latch 70 is biased by spring 82 into its locked position 71. The upper surface of the latch 70 now abuts the lower surface of the rim 105 of the container 100. The information device 10 and portable container 100 are now in the closed and locked positions 130 and 71, which prevents the container from inappropriate opening.

The workstation 220 can also be used to aid in manually preparing a fluid bag 170 for administering to the predetermined patient as in FIG. 13. Various medications are prepared and mixed in fluid bag 170. Once the medication is mixed and the fluid bag is filled, securing device 154 is placed around the fluid bag tip 172 of the fluid bag. The information device 10 is then attached in locked position 71 to the securing device 154 to prevent the inappropriate use of the fluid bag 170.

Information device 10 contains portions of dispensed medication information 580 regarding each medication mixed in fluid bag 170. Dispensed medication information 580 can be written to information device 10 by workstation 220 as each medication is mixed as part of the dispensing signal. Workstation 220 is used to transfer portions of selected patient information 520 and predetermined healthcare worker information 560 to information device 10. This transfer of the selected patient identification information is done either at the time the medication is mixed in fluid bag 170 or before the fluid bag is transported to the patient to whom it is to be administered. In this manner, medication is premixed in fluid bag 170 and stored in a convenient location so that healthcare worker 330 has quick access to the premixed fluid bag, yet portions of predetermined patient information 520 can still be added to information device 10 prior to transportation to the specific patient 360.

Communication port 288 is used to read dispensed medication information 580 stored in the information device 10 previously attached to a fluid bag 170 containing premixed medication. Healthcare worker 330 then uses workstation 220 to communicate with pharmacy system 250 to verify that the medication in fluid bag 170 has been prescribed for the predetermined patient. The workstation 220 will inform the healthcare worker 330 if the medication in fluid bag 170 is prescribed for the selected patient and alert healthcare worker 330 if it is not. If it is intended for the selected patient, workstation 220 can transmit a supplemental signal containing the selected predetermined patient information 520 to information device 10.

Container 100 or fluid bag 170 with securing device 154 are now secured and locked in closed position 130 by information device 10, and are ready for transport to a specific patient 360 in a particular hospital room 380.

Patient Verification System

Figure 15:
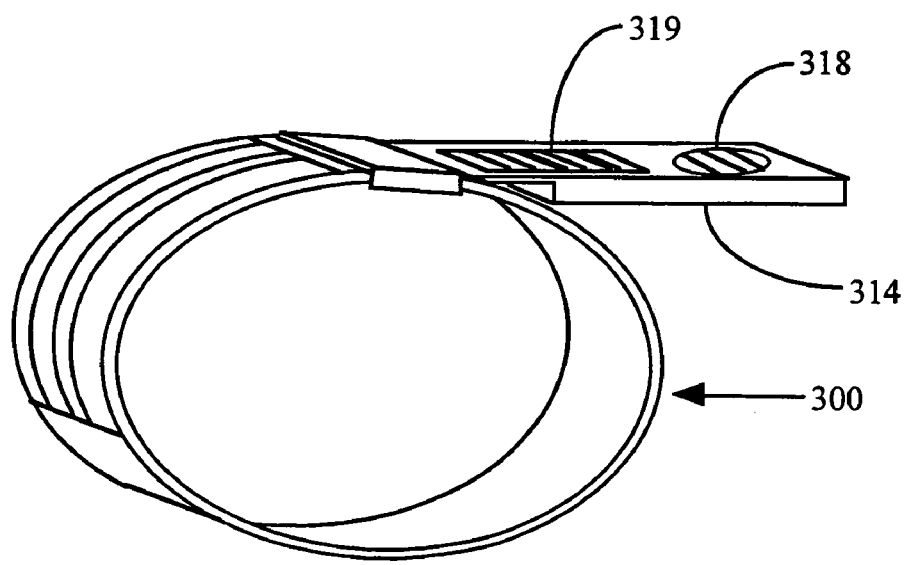
FIG. 15 is a perspective view of a patient identification device.
Figure 16:
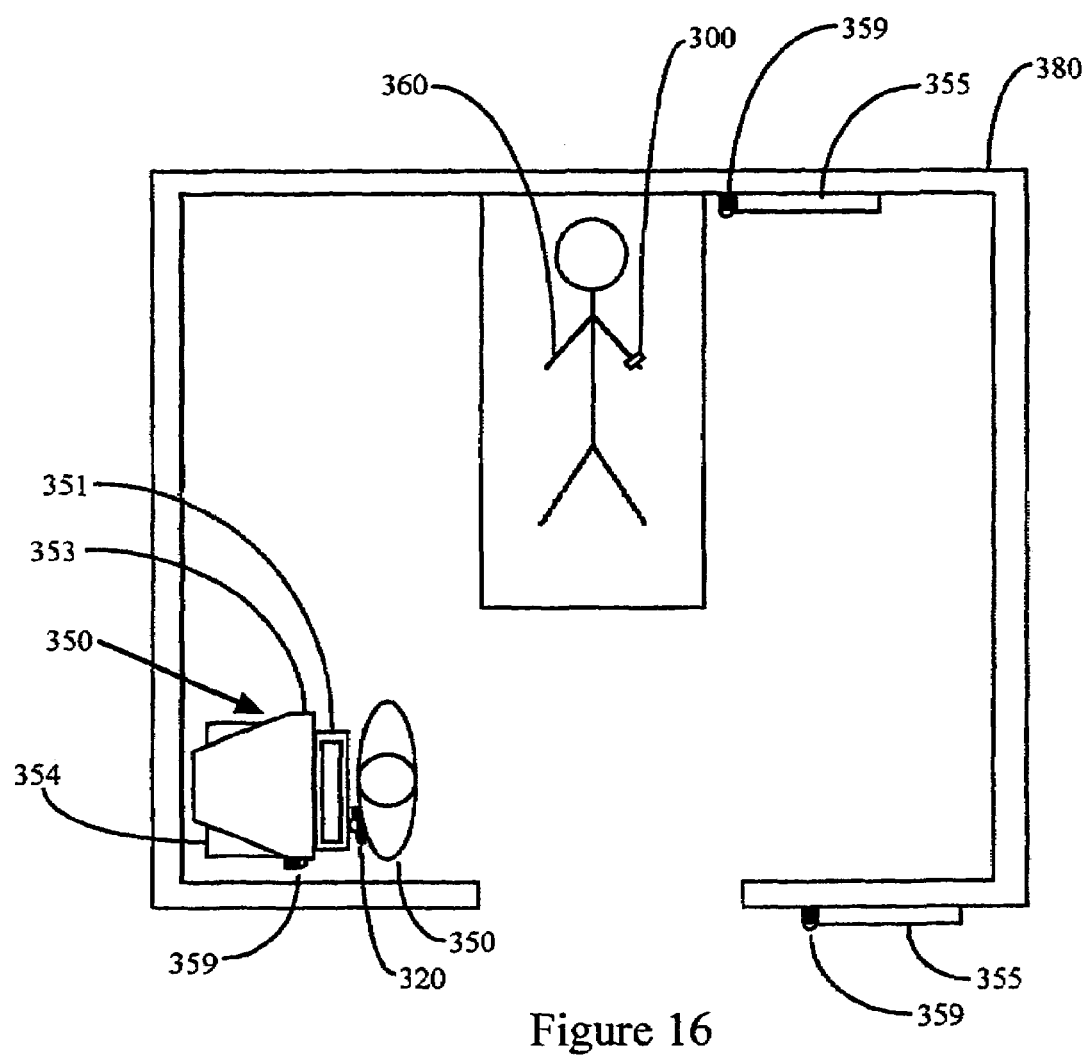
FIG. 16 is an overhead plan view of a hospital room with a specific patient in a bed and an administering healthcare worker at an information station containing a computer and electronic equipment.
Figure 29A:
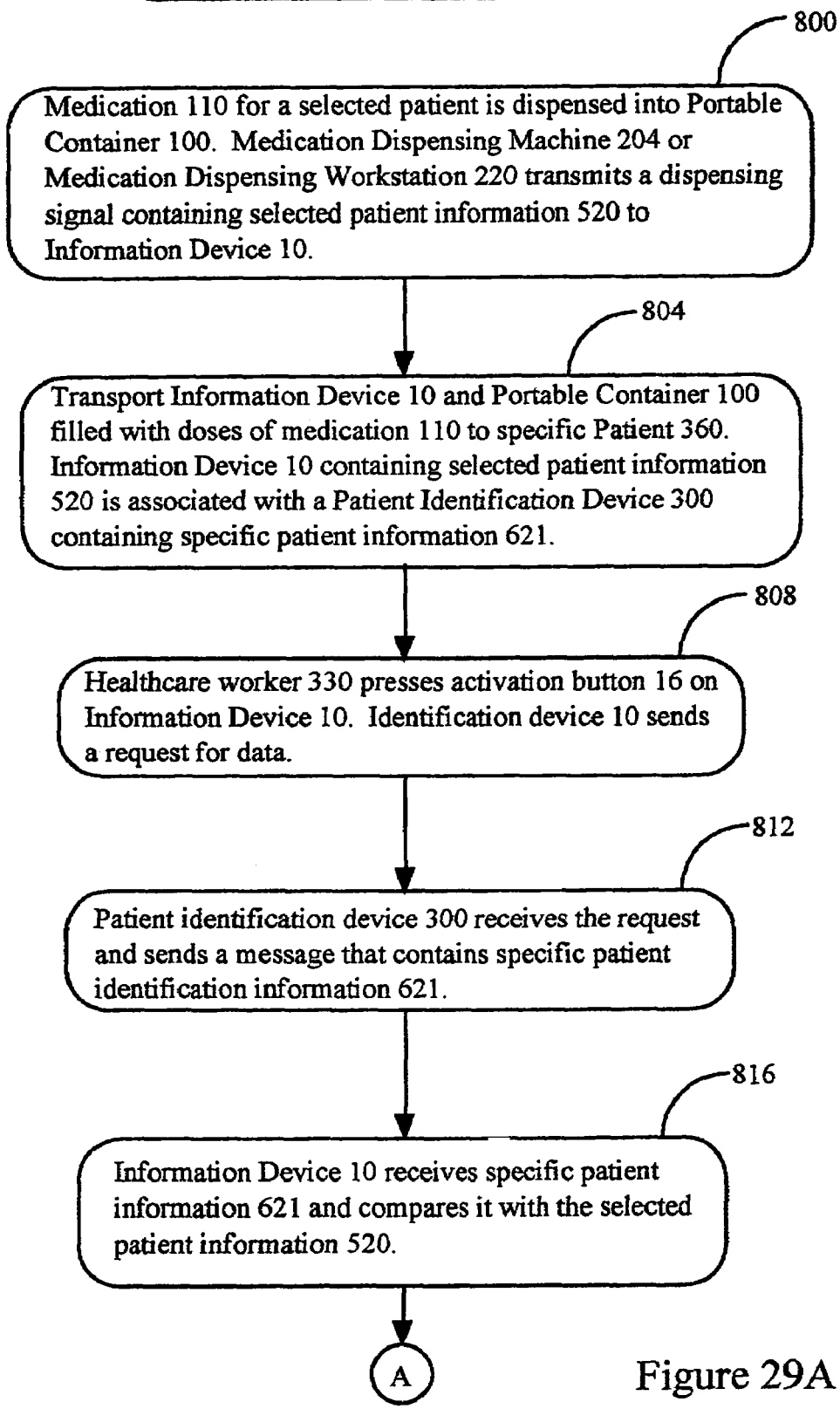
FIGS. 29A and 29B are a flowchart showing the steps in verifying that medication is administered to the specific patient for whom the medication was prescribed as in a patient verification system.
Figure 29B:
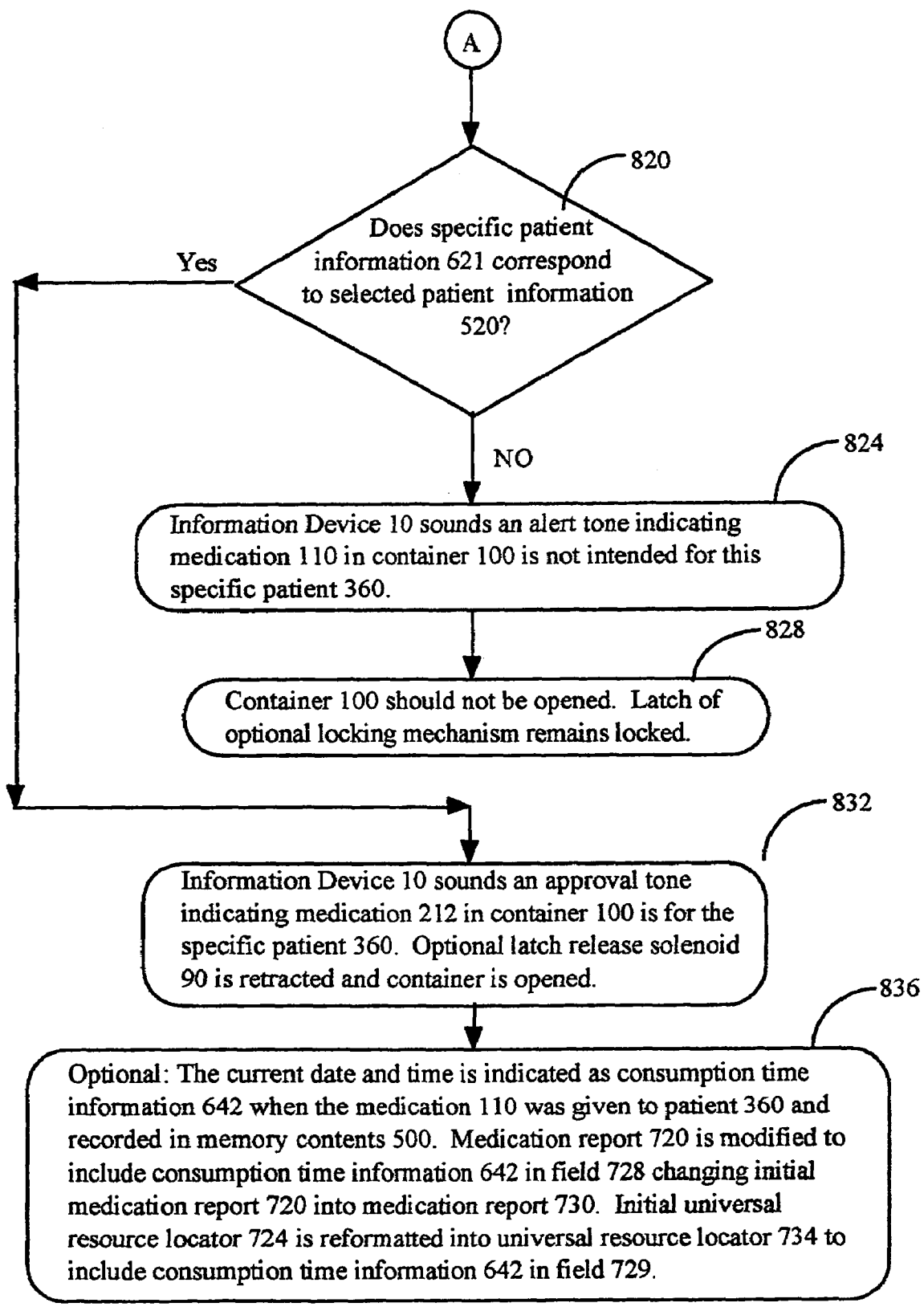

A patient verification system is accomplished by providing the specific patient 360 with patient identification device 300 as in FIGS. 15 and 16. Patient identification device 300 can take the form of a wrist bracelet. Patient identification device 300 may include a processor 314 and a communicating device 318 that is compatible with the information device 10. Memory contents 620 is held in a memory of processor 314. FIG. 20 provides a list of information contained in the memory of the patient identification device 300. Memory contents 620 can include specific patient information 621, such as patient identification number 622, patient name 623, list of medications to which patient is allergic 624, admitting physician 625, and patient blood type 626. While specific patient information 621 is shown as a list of data, the list is may include additional data elements or fewer than shown. Preferably specific patient information 621 contains at least patient identification number 622. Such information may also or alternatively be stored in bar code or magnetic strip form, such as on a bar code label 319 attached to the identification device 300. A flowchart showing a series of steps 800–836 for performing the patient verification system is shown in FIGS. 29A and 29B.

Communicating device 318 transmits specific patient information 621 for the specific patient 360 (step 800). When container 100 and attached information device 10 are brought near to patient identification device 300 (step 804), healthcare worker 330 presses activation button 16 (step 808). This causes information device 10 to transmit a signal that is received by the patient identification device 300. Patient identification device 300 responds by transmitting a verification signal containing the specific patient information 621 that is received by the information device 10 (step 812). (Alternatively, information may be read from the identification device 300 by the information device 10 using a bar code reader, magnetic strip reader, or the like.) The computer processor or comparison device 50 of the information device 10 compares portions of specific patient information 621 with corresponding elements of selected patient information 520 stored in the memory contents 500 of the information device (step 816). While the specific patient information 621 is stated to be transmitted to the information device 10 for comparison with the selected predetermined patient information 520, it should be understood that this information could be transmitted to a different comparison device such as a healthcare worker identification device 320, an information workstation 350, or a computer peripheral device 355 for comparison.

When specific patient information 621 corresponds to predetermined patient information 520 (step 820), information device 10 provides an approval tone using the audible alert device 18 to indicate that the prescribed dose of medication 110 in portable container 100 are intended for that specific patient 360 (step 832), and latch release solenoid 90 is activated to enable securing latch 70 to be released into unlocked position 72 by healthcare worker 330. Once released, the alignment projection 24 of the information device 10 is removed from opening 126 of container 100 so that the lid 122 can be moved to its open position 132. The term "corresponds to" means that the portion of information being compared matches, agrees with, falls within a range prescribed by, or correlates to the information to which it is being compared.

The real time clock 66 in the information device 10 is used to record consumption time information (e.g., date and time portable container opened information) 642 (step 836). This date and time information corresponds to when the medication 110 is given or administered to the specific patient 360. This consumption time information 642 is recorded in the memory element 62 of the information device 10 as part of consumption information 640. Medication report 720 and universal resource locator 724 are modified to include the date and time container opened information 642 in fields 728 and 729 to create a final medication report 730 as shown in FIG. 26, and the final universal resource locator 734 part of medication report components 670 as in FIG. 27.

When specific patient information 621 differs from or does not correspond to the selected patient information 520, an error tone is sounded by audible alert device 18 (step 824). Latch release solenoid 90 keeps securing latch 70 in its locked position 71 (step 828), so that the healthcare worker 330 cannot open the container 100 and give the medication to the wrong patient. The term "differs" means that the portion of information being compared does not match, agree with, fall within the range prescribed by, or correlate to the portion of information to which it is being compared.

As shown in FIG. 16, the patient verification system can be accomplished by placing a workstation 350 or computer peripheral device 355 in or near the room 380 of the specific patient 360. The workstation 350 or computer peripheral device 355 can broadcast specific patient information 621 using communication device 359 to the information device 10 on request. Workstation 350 includes input device 351, monitor 353, and processor 354. Workstation 350 or computer peripheral device 355 must be known by the healthcare worker 330 to be associated with specific patient 360 and has memory contents 690 including specific patient information 621 as in FIG. 22. This specific patient information 621 is transmitted to information device 10 as described above. The specific patient information 621 preferably includes patient identification number 622.

The patient verification system can also be accomplished by using healthcare worker identification device 320, described below, to receive specific patient information 621 from patient identification device 300, and in turn transmit this data to information device 10 to authorize the unlocking of container 100.

Healthcare Worker Authorization System

Figure 30A:
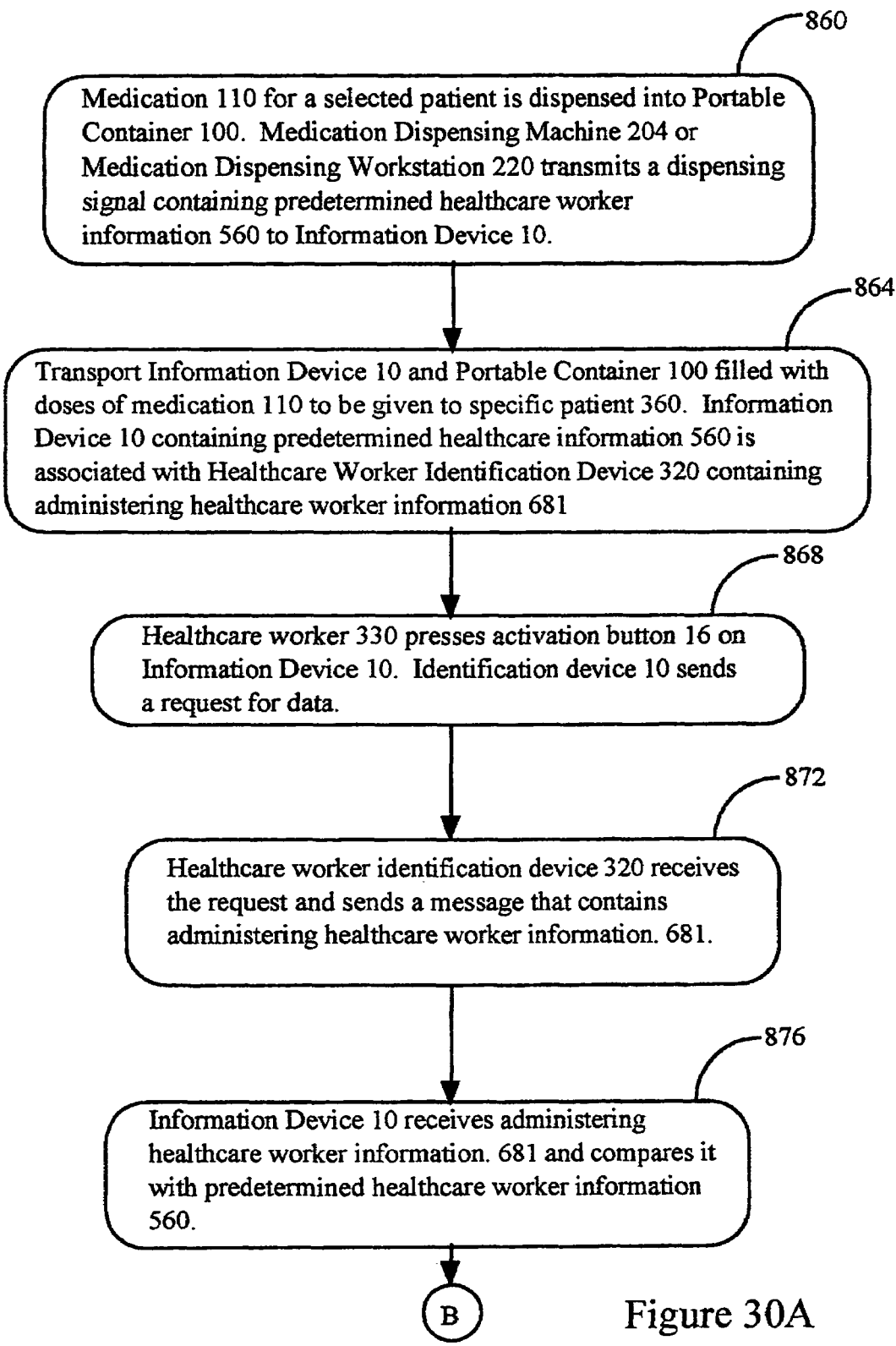
FIGS. 30A and 30B are a flowchart showing the steps in verifying that a specific healthcare worker is authorized to give medication as in a healthcare worker verification authorization system.
Figure 30B:
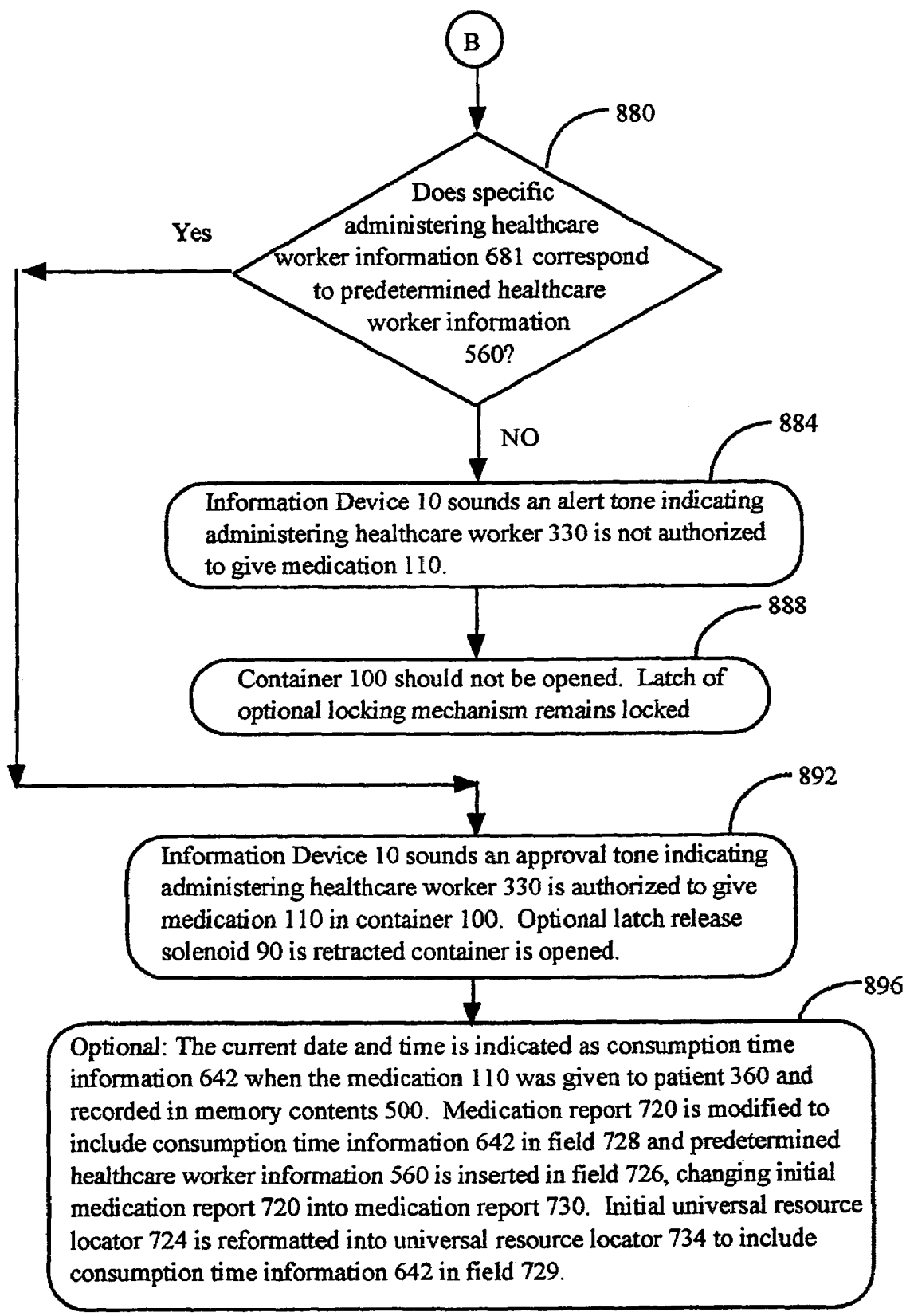

A healthcare worker authorization system can be accomplished by having healthcare worker 330 wear or carry healthcare worker identification device 320 that can communicate compatibly with information device 10. The healthcare worker identification device 320 may take the form of an identification badge as in FIG. 14. Healthcare worker identification device 320 has communication device 322, activation button 324, and processor and memory section 328. A flowchart showing a series of steps 860–896 for performing the healthcare worker authorization system is shown in FIGS. 30A and 30B.

As shown in FIG. 21, the memory contents 680 of the healthcare worker identification device 320 is held in memory of processor 328. Memory contents 680 can include administering healthcare worker information 681, such as responsibilities or title 682, identification number 683, name 684, list of patients 685 under care of healthcare worker 330. While specific administering healthcare worker information 681 is shown as a list of data, the list is may include additional data elements or fewer than shown. Preferably the data includes the responsibilities or title 682 of the healthcare worker 330. Such information may also or alternatively be stored in bar code or magnetic strip form, such as bar code label 329 attached to the identification device 320. Memory contents 680 can also include specific patient information 621 received from patient identification device 300 and final medication transaction report 660 received from information device 10.

The healthcare worker 330 is allowed to unlock the information device 10, and remove it and open portable container 100 by presenting their own administering healthcare worker information 681 to information device 10. When the portable container 100 and attached information device 10 are transported to the specific patient 360 and then brought close to healthcare worker identification device 320 (step 864), healthcare worker 330 presses activation button 16 (step 868). This causes information device 10 to transmit a signal that is received by healthcare worker identification device 320 (step 868). Healthcare worker identification device 320 responds by transmitting an authorization signal containing administering healthcare worker information 681 to information device 10 (step 872). (Alternatively, information may be read from the identification device 320 by the information device 10 using a bar code reader, magnetic strip reader, or the like.) The computer processor or comparison device 50 of the information device 10 compares portions of administering healthcare worker information 681 with corresponding elements of predetermined healthcare worker information 560 stored in the memory contents 500 of the information device (steps 876 and 880). While the administering healthcare worker information 681 is stated to be transmitted to the information device 10 for comparison with predetermined healthcare worker information 560, it should be understood that this information could be transmitted to a different comparison device such as the patient identification device 300, information workstation 350 or computer peripheral device 355 for comparison.

When administering healthcare worker information 681 corresponds to predetermined healthcare worker information 560, information device 10 provides an approval tone using the audible alert device 18 to indicate that the medication in portable container 100 can be administered to patient 360 by healthcare worker 330, and latch release solenoid 90 is activated to enable securing latch 70 to be released by healthcare worker 330 (step 892). Once released, the alignment projection 24 of the information device 10 is removed from opening 126 so that the lid 122 of the container 100 can be moved to its open position 132.

The real time clock 66 in the information device 10 is used to record consumption time information 642 indicating when the medication is given or administered to patient 360 (step 896). This consumption time information 642 is recorded in the memory element 62 of the information device 10 as part of consumption information 640. Medication report 720 and universal resource locator 724 are modified to include predetermined healthcare worker information 560 in field 726 and consumption time information 642 in fields 728 and 729 to create a final medication report 730 and a final universal resource locator 734, part of medication report components 670.

Information device 10 may be used without latch release solenoid 90. Information device 10 has one or more sensors or switches 36 or 86 to detect when container 100 is being opened. Should the healthcare worker 330 attempt to open container 100 by depressing latch release button 74 before specific patient information 621 or administering healthcare worker information 681 is transmitted to information device 10, the first switch 86 will detect the partial retraction of securing latch 70 and sound an advisory alert via audible alert device 18. Healthcare worker 330 can then allow securing latch 70 to automatically close. Should healthcare worker 330 attempt to remove information device 10 from container 100 extra sensing switch 36 detects this and sounds a more pronounced alert tone. The information device will record the inappropriate opening of container 100 for reporting at a later time.

Medication Tracking System

Figure 31A:
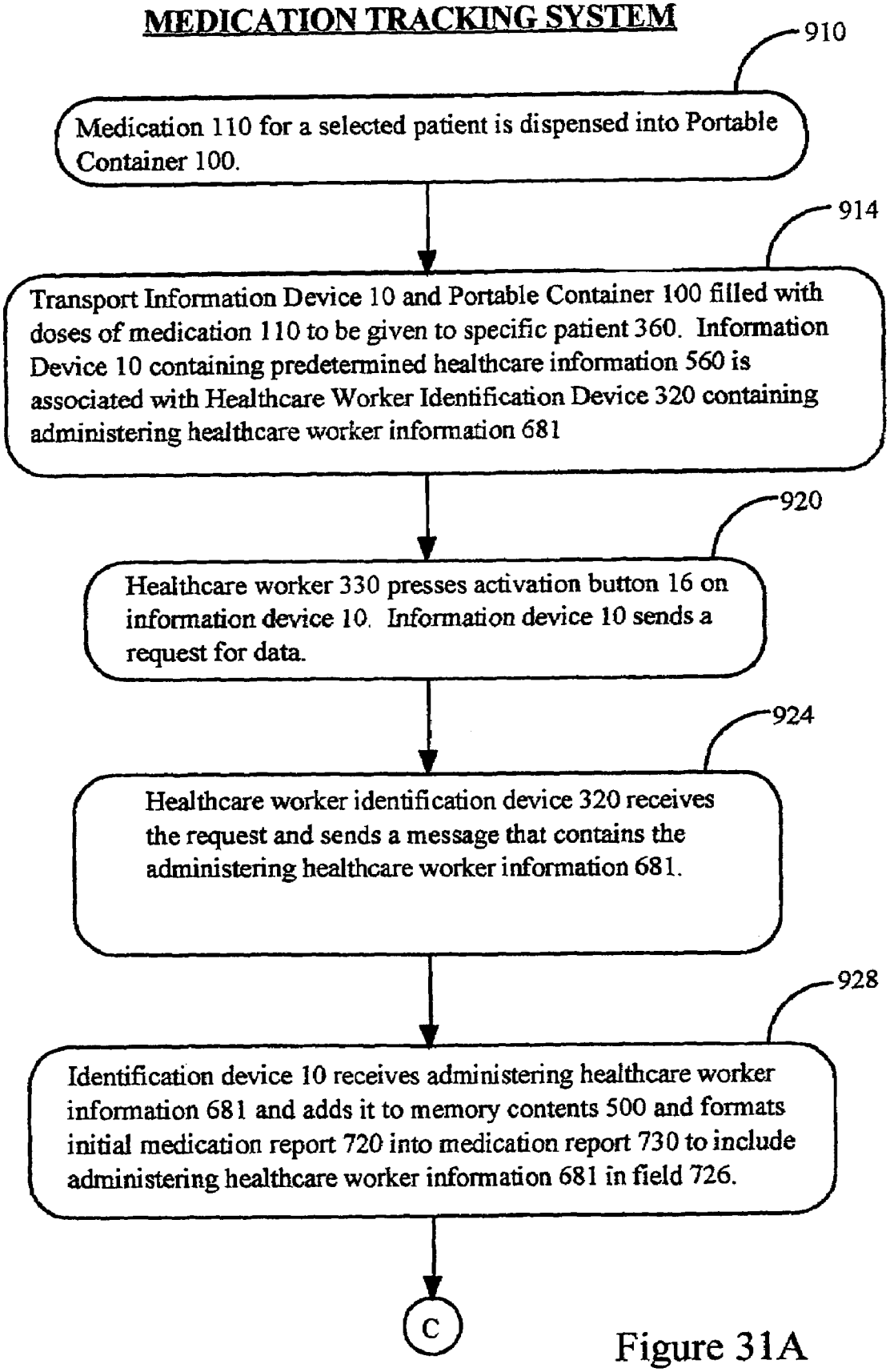
FIGS. 31A and 31B are a flowchart showing the steps in recording which healthcare worker opens a medication container as in a medication tracking system.
Figure 31B:
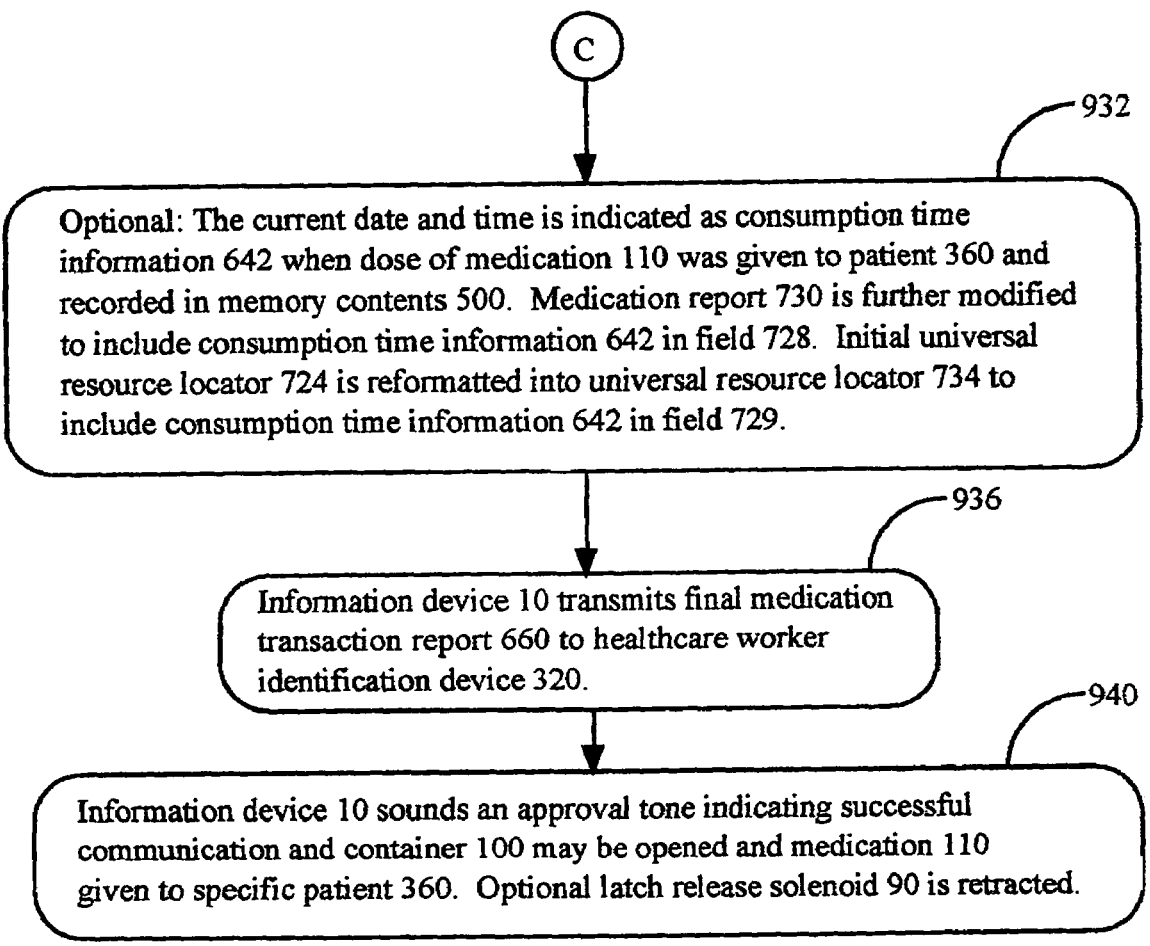

Information device can also be used as a medication tracking system. The healthcare worker 330 is allowed to unlock the information device 10, by presenting their own administering healthcare worker information 681 to information device 10. A flowchart showing a series of steps 910–940 for performing the medication tracking system is shown in FIGS. 31A–31B.

Medication 110 is dispensed into compartment 108 of container 100 for the predetermined patient using techniques discussed above (step 910). The portable container 100 and attached information device 10 are transported to the specific patient 360 (step 914) and then brought close to healthcare worker identification device 320. The healthcare worker 330 then presses activation button 16 (step 920). This causes information device 10 to transmit a signal that is received by the healthcare worker identification device 320 (step 924). Healthcare worker identification device 320 responds by transmitting an authorization signal containing administering healthcare worker information 681. Administering healthcare worker information 681 is received and is added to memory contents 500 and into field 726 of medication report 720 (step 928).

The real time clock 66 in information device 10 is used to record consumption time information 642 indicating when the medication is given or administered to patient 360 (step 932). This consumption time information 642 is recorded in the memory element 62 of the information device 10 as part of consumption information 640. Medication report 720 is further modified and universal resource locator 724 is modified to include consumption time information 642 in fields 728 and 729 to create a final universal resource locator 734 (step 932).

Information device 10 transmits final medication transaction report 660 to healthcare worker identification device 320 (step 936). Information device 10 provides an approval tone using audible alert device 18 to indicate a successful communication and that the medication in container 100 can be administered to a patient by healthcare worker 330, and the latch release solenoid 90 is activated to enable securing latch 70 to be released by healthcare worker 330 (step 940). Once released, the alignment projection 24 is pulled out of opening 126 so that lid 122 can be moved to open position 132.

Transferring Information from the Information Device to an Information System Workstation 350 or computer peripheral device 355 is also adapted to receive memory contents 500, which can be formatted as final medication transaction report 660, for automatic transfer to pharmacy system 250 or hospital information system 260. This transfer can be done by using hospital network 240. While final medication transaction report 660 is shown as a list of data in FIG. 23, the list may include additional data elements or fewer than shown.

The data in the final medication transaction report 660 may be sent preformatted to comply with the structure of the data recording system, for example, medication report 730 as shown in FIG. 26. Information device 10 may also format and transmit the address where memory contents 500 is to be stored. This may be in the form of universal resource locator (URL) 734 as shown in FIG. 27. In this case, workstation 350 need only send medication report 730 to the address indicated by universal resource locator 734 without interacting with workstation 350, thus keeping workstation 350 completely independent of needing to know how to handle medication report 730. Using the technology of the Internet, medication report 730 can be viewed on a display 740 of a workstation in a doctor's office, home or any workstation 220 or 350 as shown in FIG. 28. Using a browser or general purpose data retrieval, display, and entry program, medication report 730 may displayed by any workstation as seen in medication report browser presentation 744.

Information device 10 is returned to dispenser 204 for reuse. When this is done, memory contents 500, which can be formatted as final medication transaction report 660, is transmitted to dispenser 204 so that memory contents 500 can be communicated to pharmacy system 250 or hospital information system 260, via hospital network 240, and the information device 10 is considered available for reuse. Any error conditions, such as low battery voltage or communication errors, are also transmitted to dispenser 204 from information device 10.

Transferring Information from the Healthcare Worker Identification Device to an Information System The healthcare worker identification device 320 can also receive final medication transaction report 660 or components of it from information device 10. Final medication transaction report 660 can in turn be communicated to the workstation 350 by healthcare worker identification device 320 for communication to pharmacy database 254 or database 264 to automate the recording of the patient receiving.

Using Information Device to Label Medical Samples and Personal Items

The information device 10 can also be used to record patient information regarding blood, fluid, or tissue samples collected from a specific patient 360. A healthcare worker 330 obtains the samples directly from the specific patient 360, places them in compartment 108 and closes lid 122. Healthcare worker 330 then presses activation button 16, and information device 10 is placed in communication with the patient identification device 300 or workstation 350 associated with patient 360. In the same process as explained above, specific patient information 621 is transferred to information device 10. Healthcare worker 330 can manually press latch release button 74 and secure information device 10 to the container 100 to prevent the container from inappropriate opening. The container 100 holding the blood, fluid, or tissue sample is then transferred to the appropriate laboratory for analysis. When received by the laboratory, specific patient information 621 is transferred from information device 10 by communicating with workstation 220, now placed in a laboratory setting, or a laboratory system (not shown). The laboratory will now know from which specific patient 360 the sample came.

A similar process may be used to label a patient's personal items. A patient may enter a medical facility with many valuable personal items, such as hearing aids, jewelry, etc. These personal items are often removed from the patient during treatment. To ensure that such items are returned to the proper patient, and are not misplaced, such items may be stored in a container secured by an information device 10 as described herein. At the time that the personal items are placed in the container, patient identification information is transferred to the information device 10 from the patient identification device 300, or otherwise obtained therefrom. Healthcare worker identification information, obtained by the information device 10 from a healthcare worker identification device 320, may also be stored in the information device 10, to identify the healthcare worker who took the personal items from the patient. The information device 10 will prevent access to the items within the container, or will provide a warning indication, unless the information device 10 is presented the correct identification information from the patient identification device 300 at the time the personal items are to be returned to the patient. For additional security, conventional theft deterrent devices, such as RF detection devices, may be mounted in or on the container or the information device 10 attached thereto. These devices, in combination with a conventional theft deterrent system, may be employed to prevent the container with personal items therein from being removed from, e.g., a hospital or other area without a warning being provided.

For additional security, when specific patient information 621 is read from the identification device 300 by the information device 10, it may be accompanied by a secret code generated by the identification device 300 or the information device 10 at that time. The secret code is recorded, e.g., in the memory of the identification device 300 and the memory of the information device 10. When the container 100 is to be opened, e.g., to return items to a patient, both the patient identification information and the secret code are retrieved from the identification device 300 by the information device 10 and compared with the identification information and secret code stored therein. Access to the container is allowed only if both the retrieved identification information and retrieved secret code match the stored identification information and secret code.

Figure 34:
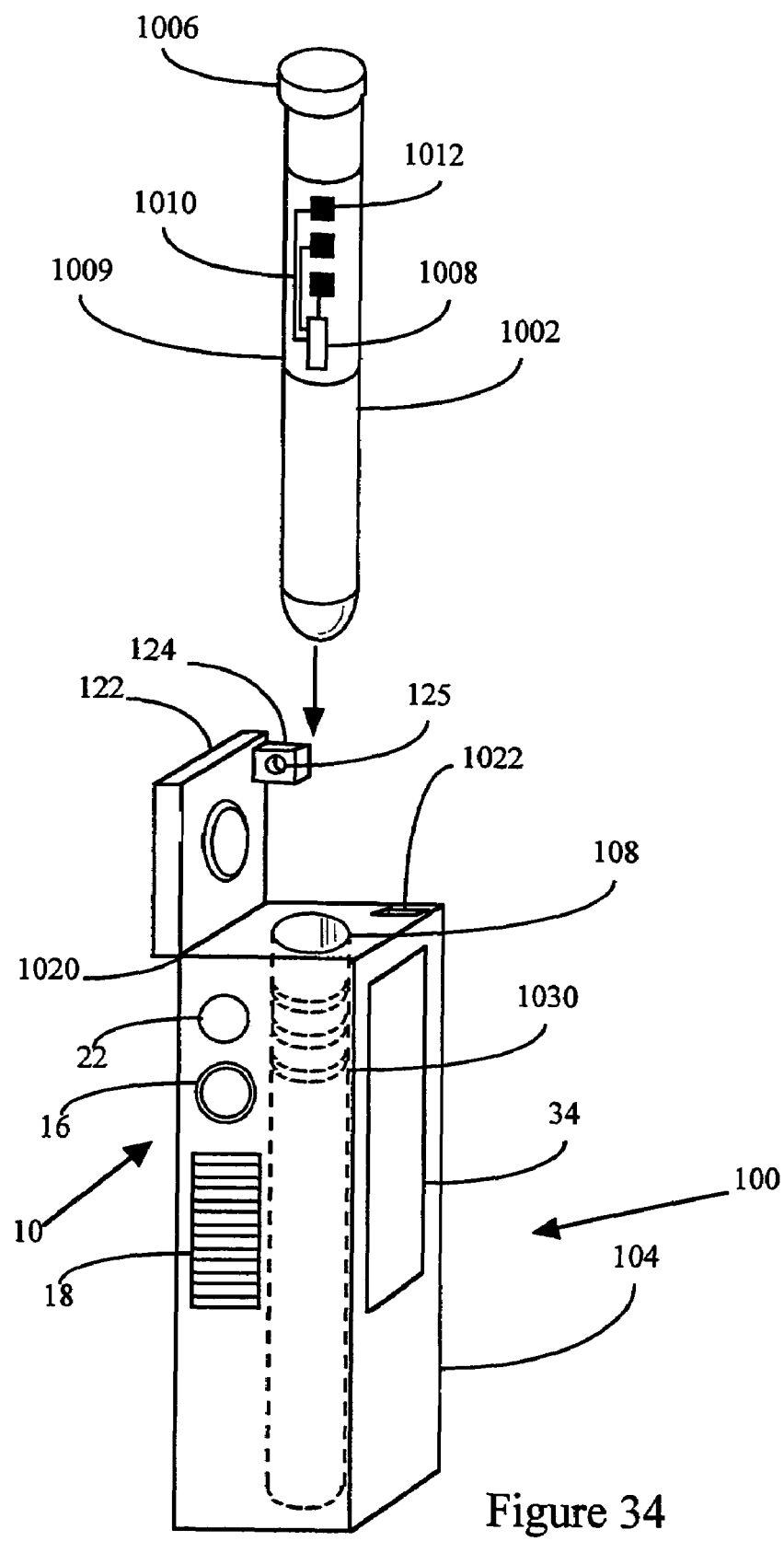
FIG. 34 shows an exemplary system for labeling and identifying medical samples in accordance with the present invention.

Another example of a system for labeling medical samples in accordance with the present invention is shown in FIG. 34. A tube or vial 1002, such as a glass tube, is used to collect blood or other specimens from a patient. (Note that the tube 1002 may be any type of container, including, e.g., a slide, etc. for holding a sample or other item.) For example, tube 1002 may be inserted into a blood syringe to withdraw blood from a patient. After the blood or other sample has been collected, the tube 1002 is closed by a cap 1006. The tube 1002 preferably has an electronic memory device 1008 attached to it. The memory device 1008 may be implemented in a form similar to that used by Smart Cards. The memory device 1008 may be attached to a flex circuit 1009 that includes electrically insulated conductors 1010 leading to exposed electrical contacts 1012. The flex circuit 1009 may be attached to the tube 1002 on the outer surface thereof with an epoxy or other adhesive.

A container 100, as described previously, may be designed to receive and hold the tube 1002. For example, container 100 may include a base 104, a compartment 108 adapted for containing the tube 1002, a lid 122, and a hinge 1020, such as a living hinge. Lid 122 may include a projecting tab 124 with a hole 125 formed therein. The tab 124 is positioned on the lid 122 so as to enter an opening 1022 in the container 100 when the lid 122 is closed. The container 100 may include an integral information device 10, similar to those previously described. The information device 10 may include an activation button 16, a transceiver 22 to read specific patient identification information 621 from a patient identification device 300, as described previously, an optional display 34, and audible alert 18 devices. The information device 10 may include a processor, battery, and memory, as described previously.

An exemplary and typical use of the system illustrated in FIG. 34 follows. After a blood or other sample has been drawn or taken, and placed within the tube 1002, the tube 1002 is capped 1006 and placed in the compartment 108 in the container 100. (Additional compartments 108 may be provided in the container 100 to hold multiple tubes 1002, or one or more large compartments may be formed in the container 100 to hold multiple tubes 1002.) Lid 122 is rotated about hinge 1020 so that projecting tab 124 enters opening 1022, thereby closing the tube 1002 within the compartment 108. A healthcare worker may then press activation button 16 such that information device 10 is placed in communication with a patient identification device 300. In the same process as described previously, specific patient information 621 is transferred from the patient identification device 300 to the information device 10. Such patient information may be displayed on display 34. The information device 10 may also issue an audible acceptance tone using alert device 18 and activate a locking mechanism to lock the lid 122 closed. (The locking mechanism may include a solenoid which is activated to extend into hole 125 formed in the projecting tab 124 to secure the lid 122 to the base 104 of the container 100.) The sample contained in the tube 1002, within the container 100, will be sent to, for example, a laboratory for analysis, bearing the specific patient information 621 from the patient information device 300 in a manner that ensures that the sample will not be confused with a sample from another patient. When the container 100 is received in the laboratory, the specific patient information 621 may be read from the information device 10 positively to identify the patient from whom the sample was drawn.

The compartment 108 formed in the container 100 may be equipped with electrical contacts 1030 designed to mate with the contacts 1012 formed on the tube 1002 when the tube 1002 is placed in the compartment 108. When information device 10 reads specific patient information 621 from an identification device 300, a portion of this information can be written by the information device processor, via contacts 1030 and 1012, to memory device 1008 mounted on the tube 1002. The date and time can also be written to the memory device 1008 by the information device 10. As previously discussed, transceiver 22 can also be used to read healthcare worker information 681 from a healthcare worker identification device 320. The information device 10 may also transfer a portion of this information to the memory device 1008 on the tube 1002. Thus, all necessary identification information may be provided in the memory device 1008 mounted on the tube 1002 itself. Therefore, the information device 10 itself need not include memory of its own for storing such information. When the laboratory removes the tube 1002 from the container 100 for analysis, the laboratory will be able to identify, e.g., which patient the sample came from, the time it was drawn, and who drew the sample, from memory device 1008 mounted on the tube itself.

As a further enhancement, the information device 10 may be previously programmed with selected patient information 520, the type of sample that is to be obtained, and the type of laboratory analysis to be performed on the sample. Compartment 108 may contain one or more empty tubes 1002. Container 100 is brought to the patient and transceiver 22 is used to read specific patient information 621 from a patient identification device 300. A comparison is performed between selected patient information 520 and specific patient information 621. If there is a match, the lid 122 of the container 100 may be allowed to be opened such that the healthcare worker can remove the tube 1002 for use. The type of sample that is to be obtained may be displayed at this time on the display 34.

Updating of Information Relating to Container Contents

An information device 10 attached to a container 100 may preferably be adapted to receive updated information relating to the contents of the container. Such communication may be accomplished in a conventional manner via direct or wireless connection between the information device and a computer network. (Such communications may be received by the information device 10 via the internal communication device 22 or via a separate communication device for receiving such communications.) The updated information relating to the contents of the container may indicate a required change to the container contents. The information device 10 may display such a required change, e.g., on display 34, or provide an audible or other visual indication indicating such a required change. Such a display or indication may be provided when the information is received, when the container is to be opened, or when an identification verification is attempted or performed.

For example, as discussed previously, a container 100 may include medication and an attached information device may include dispensed medication information 580 stored therein. If a patient's prescription changes, e.g., medication is to be added or deleted, after the medication is dispensed into the container, but before the medication is delivered to the patient, this required change may be communicated to the information device, and presented to a health care worker. Thus, a patient can be assured to receive the proper prescription. Information concerning required changes to other information, such as the timing of providing medication to a patient, may also be communicated to the information device.

Infusion Pump Control

Figure 33:
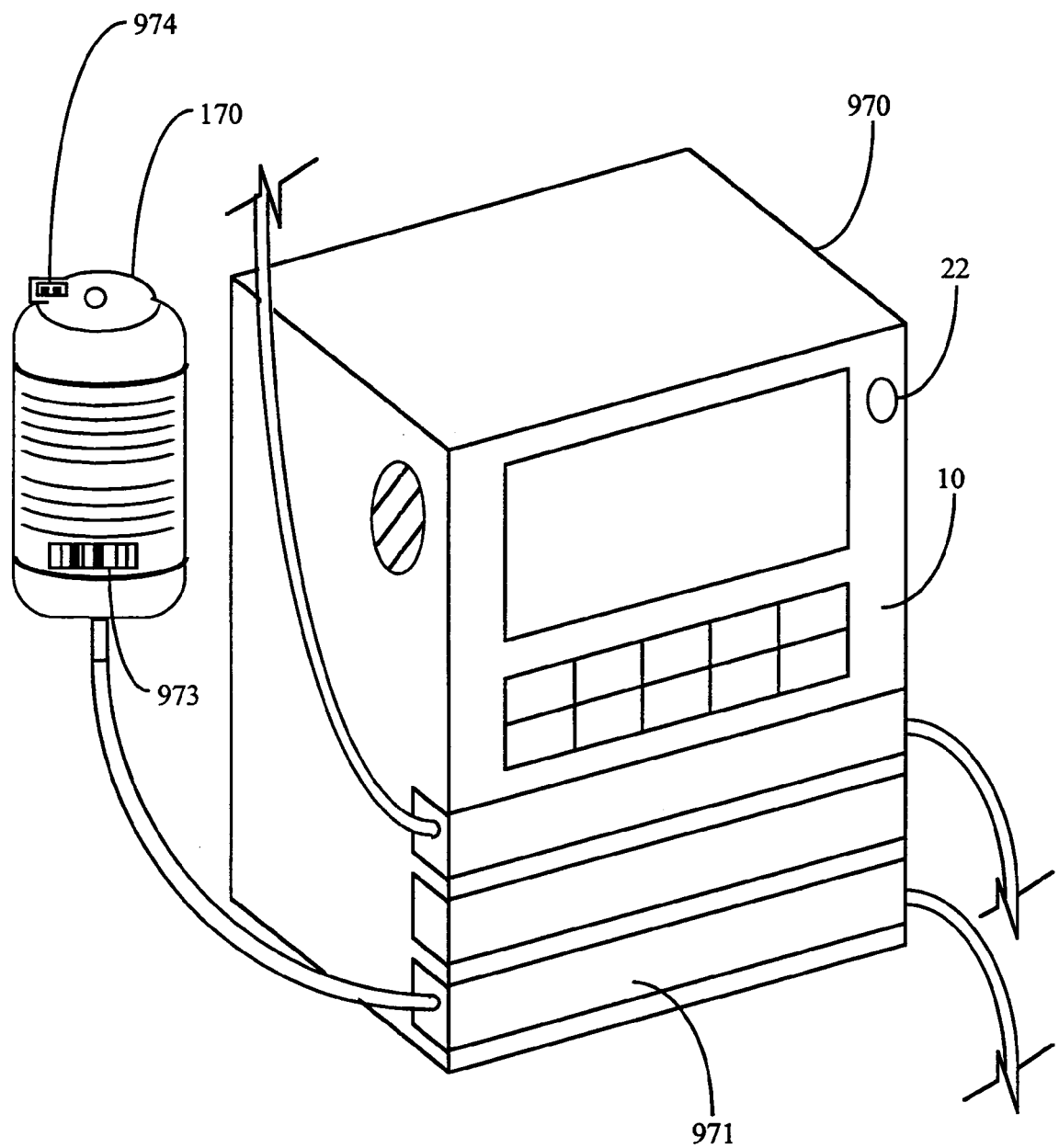
FIG. 33 shows an apparatus including a system for dispensing intravenous fluids according to one embodiment of the invention.

In an alternate embodiment of the invention, as shown in FIG. 33, the information device 10 may be connected to or integrally formed as part of a fluid dispensing system, such as an infusion pump 970. In the event that the information device identification information 520 and the identification device identification information 621, obtained from a patient identification device 300, correspond correctly to each other, then the information device 10 can activate a response function in the form of, e.g., allowing the infusion pump motor to operate to dispense fluid from an IV bag 170, unlocking a compartment 971 on the infusion pump 970 to allow the IV bag 170 to be mounted thereon, and/or providing an audible or visual indication, as discussed previously. Healthcare worker information 681 also may be required to be transferred from a healthcare worker identification device 320 to information device 10, and a comparison performed, in the manner described previously, to determine if the healthcare worker is authorized to operate the infusion pump 970.

In another preferred embodiment, an information device 10 in accordance with the present invention, which is separate from the infusion pump 970, may be employed as part of an infusion pump control system. The infusion pump 970 may include a conventional infusion pump controller which controls, e.g., the flow rate and flow duration from the IV bag 170 (or multiple IV bags). A conventional receiver/transmitter, similar to the receiver/transmitter 22, may be provided in the infusion pump 970 for allowing infusion pump control information (for example, flow rate, duration, and IV type) to be received by the infusion pump controller. The information device 10 may have such infusion pump control information stored therein, and may communicate such information, via the communication device 22, to the infusion pump controller. The information device 10 may be attached to the IV bag 170, as shown, for example in FIG. 7 or the IV bag 170 put in a container including an information device, as shown in FIG. 10. Alternatively, the infusion pump control information, including information identifying for whom the IV 170 is prescribed, may be provided on the IV bag 170 itself, e.g., in the form of a bar code label 973 or memory device 974, such as a conventional RF identification device or solid state memory device, mounted on the IV bag in a conventional manner. In such a case, the information device 10 mounted in the infusion pump would include a conventional device, e.g., a bar code reader, RF identification device reader, etc., for reading the identification information from the IV bag 170. The information device 10 and IV bag 170 (or just the IV bag 170, if the infusion pump control information is provided directly thereon) are transported to the infusion pump where the infusion pump control information is downloaded from the information device 10 (or obtained from the IV bag 170 bar code 973 or memory device 974) into the infusion pump controller, and the IV bag 170 is attached to the infusion pump 970. (A comparison of patient identification information stored in (or on) the information device with patient identification information stored in the infusion pump controller may also be performed, in the manner described above. In this case, the infusion pump controller acts as a peripheral identification device 355 having memory contents including specific patient information.) The infusion pump controller may provide a confirmation indication and/or a signal to the information device 10 that the desired infusion pump control information was received. This confirmation information may be recorded in the information device 10 for later transmission to a database, as described above. Alternatively, the information device 10 may merely store the fact that the infusion pump control information was communicated to the infusion pump controller.

This system may be employed in combination with the identification verification system described above, to ensure that the correct patient receives the correct IV prescription. For example, an information device 10 attached to, or otherwise associated with, an IV bag 170, may include infusion pump control information, including information identifying for whom the IV 170 is prescribed. (Alternatively, as discussed above, such information may be provided by a bar code 973 or memory device 974 mounted on the IV bag 170 itself.) Such information may be read into and stored in the infusion pump controller at the time the IV bag 170 is mounted on the infusion pump 970 and the IV is administered to the patient. As subsequent replacement or additional IV bags 170 are brought to the infusion pump 970, the infusion pump control information, including patient identification information, associated therewith, is obtained by the infusion pump controller. The infusion pump controller, acting as an information device, compares the patient identification information thus obtained with the patient identification information obtained from the first IV bag 170 (e.g., from the information device 10 attached thereto) which was provided to the infusion pump 970. In the event that the identification information corresponds correctly to each other, the infusion pump controller/information device can activate a response function to, e.g., allow the subsequent IV bag 170 to be mounted on the infusion pump 970, allow the infusion pump 970 to dispense fluid from the subsequent IV bag 170, and/or provide an audible or visual (or other) indication. Thus, in this manner, the first IV bag 170 attached to the infusion pump 970 includes patient identification information associated therewith which is read into and stored in the infusion pump information device, to thereby effectively assign the infusion pump 970 for use by a single patient, and no other, thereby assuring that a patient will receive correct IV prescriptions.

Applications in Other Fields

Although the above-described apparatus is of particular use in medical and hospital administration applications, its advantages can be utilized in other fields as well. For example, a verification apparatus in accordance with the present invention may be especially useful in an industrial setting where individual components are shipped from one location to another. As a system for tracking the location and access to certain components, the verification apparatus contains an information device 10, an identification device 300, and a container 100. Industrial components may be locked in the container 100 by a locking mechanism controlled by the information device 10. When an individual wishes to retrieve the components from the container 100, the identification device 300, including identification device identification information 621, is presented to the information device 10. The information device 10 proceeds to compare its own information device identification information 520 with the identification device identification information 621. If the two pieces of information correspond to each other, then a response signal is activated. In one embodiment of the invention, the response signal activates the unlocking of the container 100. Alternatively, or additionally, the response signal may control an audible or visual indication.

It should also be understood that the roles of the information device and identification device described herein may be interchanged for some activities. For example, identification information may be sent from an information device to an identification device, with the comparison of information described above performed in the identification device. If the identification comparison is favorable, the identification device may issue an audible or visual alert and/or send a response signal to the information device to provide an alert and/or unlock the lid of a container.

While the invention has been described with reference to a preferred embodiment, it will be understood by those skilled in the art that various changes may be made and equivalents may be substituted without departing from the broader aspects of the invention.

What is claimed is:

1. A verification apparatus, comprising:
    an identification device including identification device identification information;
    a portable information device adapted to provide a response signal and having information device identification information stored therein and adapted to obtain identification device identification information from the identification device;
    a portable locking mechanism connected to the portable information device;
    wherein the information device compares the information device identification information stored therein to the identification device identification information obtained from the identification device and provides the response signal if the identification device identification information corresponds to the stored information device identification information; and wherein the response signal provided by the portable information device controls the portable locking mechanism to unlock the locking mechanism when the identification device identification information corresponds to the stored information device identification information.

2. The verification apparatus of claim 1, wherein the identification device includes identification device identification information stored therein and is adapted to communicate the identification device identification information to the portable information device and wherein the portable information device is adapted to receive the identification device identification information communicated thereto.

3. The verification apparatus of claim 1, wherein the identification device includes identification device identification information provided thereon and wherein the portable information device is adapted to read the identification device identification information from the identification device.

4. The verification apparatus of claim 3, wherein the identification device includes identification information provided thereon in bar code form.

5. The verification apparatus of claim 1, wherein the portable information device and the portable locking mechanism are integrally formed with each other.

6. The verification apparatus of claim 1, comprising additionally a container connected to the locking mechanism, the locking mechanism controlling access to an interior of the container.

7. The verification apparatus of claim 6, wherein the container includes a base portion including the interior of the container and a lid adapted to be opened to allow access to the interior of the container and to be closed over the base portion to prevent access to the interior of the container and wherein the locking mechanism is attached to the container so as to prevent the lid from being opened when the locking mechanism is locked.

8. The verification apparatus of claim 6, wherein the locking mechanism is formed integrally with the container.

9. The verification apparatus of claim 1, comprising additionally a fluid flow control device connected to the locking mechanism, the locking mechanism controlling a flow of fluid past the fluid flow control device.

10. The verification apparatus of claim 9, wherein the fluid flow control device includes first and second clamping portions adapted to be clamped around an extending tip of a fluid bag to prevent a flow of fluid therefrom and wherein the locking mechanism is attached to the fluid flow control device so as to prevent the first and second clamping portions from being unclamped when the locking mechanism is locked.

11. The verification apparatus of claim 1, comprising additionally an indicator to provide an indication connected to the portable information device and wherein the response signal provided by the portable information device controls the indicator to provide the indication if the identification device identification information corresponds to the stored information device identification information.

12. The verification apparatus of claim 11, wherein the indicator is controlled by the response signal to provide an indication selected from the group of indications consisting of visual and audible indications if the identification device identification information corresponds to the stored information device identification information.

13. The verification apparatus of claim 11, comprising additionally a portable container and wherein the indicator and the information device are formed integrally with the portable container.

14. The verification apparatus of claim 11, wherein the indicator is adapted to provide an alert indication and wherein the alert indication is activated by the information device when the information device identification information does not correspond to the identification device identification information.

15. The verification apparatus of claim 1, further comprising:
data entry means adapted to communicate with the information device for modifying the information device identification information stored in the information device.

16. The verification apparatus of claim 1, further comprising an alert device, the alert device being activated by the information device when the information device identification information does not correspond to the identification device identification information.

17. A verification apparatus, comprising:
an identification device including identification device identification information;
a portable information device adapted to provide a response signal and having information device identification information stored therein and adapted to obtain identification device identification information from the identification device;
wherein the information device compares the information device identification information stored therein to the identification device identification information obtained from the identification device and provides the response signal if the identification device identification information corresponds to the stored information device identification information;
an indicator to provide an indication connected to the portable information device and wherein the response signal provided by the portable information device controls the indicator to provide the indication if the identification device identification information corresponds to the stored information device identification information; and
wherein the indicator is formed integrally with the portable information device.

18. A verification apparatus, comprising:
an identification device including identification device identification information;
a portable information device adapted to provide a response signal and having information device identification information stored therein and adapted to obtain identification device identification information from the identification device;
data entry means adapted to communicate with the information device for modifying the information device identification information stored in the information device wherein the data entry means is integrally connected to the information device;
wherein the information device compares the information device identification information stored therein to the identification device identification information obtained from the identification device and provides the response signal if the identification device identification information corresponds to the stored information device identification information.

19. The verification apparatus of claim 18, wherein the identification device is an object identification device and wherein the information device identification information and the identification device identification information identify an object which must be identified for the response signal to be provided.

20. The verification apparatus of claim 19, wherein the identification device is a patient identification device and wherein the information device identification information and the identification device identification information identify a patient which must be identified for the response signal to be provided.

21. The verification apparatus of claim 19, wherein the identification device is a worker identification device and wherein the information device identification information and the identification device identification information identify a worker which must be identified for the response signal to be provided.

22. A verification apparatus, comprising:
an identification device including identification device identification information;
a portable information device adapted to provide a response signal and having information device identification information stored therein and adapted to obtain identification device identification information from the identification device;
wherein the information device compares the information device identification information stored therein to the identification device identification information obtained from the identification device and provides the response signal if the identification device identification information corresponds to the stored information device identification information;
a second identification device including second identification device identification information and wherein the information device is adapted to obtain the second identification device identification information from the second identification device, and wherein the information device includes second information device identification information stored therein and compares the second information device identification information stored therein to the second identification device identification information obtained from the second identification device and provides the response signal if the second identification device identification information corresponds to the stored second information device identification information.

23. The verification apparatus of claim 22, further comprising a display module for displaying information stored in the information device.

24. The verification apparatus of claim 22, comprising additionally a container connected to the information device.

25. The verification apparatus of claim 24, wherein the interior of the container is large enough to hold an IV fluid bag.

26. The verification apparatus of claim 24, wherein the interior of the container is large enough to hold a plurality of personal items.

27. The verification apparatus of claim 24, wherein the interior of the container is adapted to hold a medical sample tube.

28. The verification apparatus of claim 24, wherein the container is a portable container.

29. The verification apparatus of claim 28, wherein the portable information device is formed integrally with the portable container.

30. The verification apparatus of claim 24, further comprising:
data entry means adapted to communicate with the information device for modifying the information device identification information stored in the information device.

31. The verification apparatus of claim 30, wherein the data entry means includes a dispensing system including a database of information identifying objects to be dispensed into the container and corresponding identification information used to modify the information device identification information stored in the information device.

32. The verification apparatus of claim 31, wherein the dispensing system is an automatic dispensing system for dispensing objects into the container.

33. The verification apparatus of claim 24, wherein the information device includes information about contents of the interior of the container stored therein.

34. The verification apparatus of claim 33, further comprising an input device for transmitting information about the contents of the interior of the container to the information device.

35. The verification apparatus of claim 24, wherein the information device includes a communication device for receiving information relating to a required change to the contents of the container.

36. The verification apparatus of claim 35, wherein the container has an interior adapted to hold prescription medication and wherein the information received relating to a required change to the contents of the container is a change in a prescription.

37. The verification apparatus of claim 35, wherein the information device includes a display device and wherein a message is displayed on the display device relating to the information received relating to a required change to the contents of the container.

38. The verification apparatus of claim 35, wherein the providing of the response signal is disabled in response to the receipt of the information relating to a required change to the contents of the container.

39. A verification apparatus, comprising:
an identification device including identification device identification information;
a portable information device adapted to provide a response signal and having information device identification information stored therein and adapted to obtain identification device identification information from the identification device;
a container connected to the information device;
data entry means adapted to communicate with the information device for modifying the information device identification information stored in the information device, wherein the data entry means is integrally connected to the container;
wherein the information device compares the information device identification information stored therein to the identification device identification information obtained from the identification device and provides the response signal if the identification device identification information corresponds to the stored information device identification information.

40. A verification apparatus, comprising:
an identification device including identification device identification information;
a portable information device adapted to provide a response signal and having information device identification information stored therein and adapted to obtain identification device identification information from the identification device;
a container connected to the information device;
a sensor for detecting when the container is opened and wherein the information device is connected to the sensor for detecting when the container is opened and includes memory means for storing information provided by the sensor indicating that the container was opened;
wherein the information device compares the information device identification information stored therein to the identification device identification information obtained from the identification device and provides the response signal if the identification device identification information corresponds to the stored information device identification information.

41. The verification apparatus of claim 40, wherein the information device includes a communication device for transmitting the information stored in memory indicating that the container was opened to a database.

42. The verification apparatus of claim 40, further comprising a clock for providing time information and wherein the information device is connected to the clock and includes memory means for storing time information provided by the clock in response to the sensor when the container is opened.

43. The verification apparatus of claim 42, wherein the information device includes a communication device for transmitting the time information stored in memory when the container is opened to a database.

44. A verification apparatus, comprising:
an identification device including identification device identification information;
a portable information device adapted to provide a response signal and having information device identification information stored therein and adapted to obtain identification device identification information from the identification device;

a container connected to the information device wherein the container includes a plurality of distinct interior sections wherein the information device compares the information device identification information stored therein to the identification device identification information obtained from the identification device and provides the response signal if the identification device identification information corresponds to the stored information device identification information.

46. The verification apparatus of claim 44, wherein the information device includes stored information relating to selected interior sections of the container.

46. The verification apparatus of claim 45, wherein the stored information relating to selected interior sections of the container is identification information and wherein the information device compares the stored identification information relating to the selected interior sections of the container to the identification information obtained from the identification device and provides selected response signals when the identification information relating to selected interior sections of the containers corresponds to the identification information obtained from the identification device.

47. The verification apparatus of claim 46, wherein the plurality of interior sections have separate locking mechanisms associated therewith, and wherein selected ones of the locking mechanisms are adapted to unlock access to selected ones of the plurality of interior sections of the container in response to the providing of the selected response signals.

48. The verification apparatus of claim 46, wherein the plurality of interior sections have separate indicators associated therewith, and wherein selected ones of the indicators are adapted to provide an indication in response to the providing of the selected response signals.

49. A verification apparatus, comprising:

an identification device including identification device identification information;

a portable information device adapted to provide a response signal and having information device identification information stored therein and adapted to obtain identification device identification information from the identification device;

wherein the information device compares the information device identification information stored therein to the identification device identification information obtained from the identification device and provides the response signal if the identification device identification information corresponds to the stored information device identification information; and an infusion pump connected to the information device, and wherein the infusion pump is enabled for operation in response to the response signal.

50. The verification apparatus of claim 49, wherein the information device is integrally formed with the infusion pump.

51. The verification apparatus of claim 49, comprising additionally an IV bag and wherein the identification device is attached to the IV bag.

52. The verification apparatus of claim 51, wherein the identification device attached to the IV bag is selected from the group of identification devices including a bar code and a memory device.

53. A verification apparatus, comprising:

a portable container having an interior adapted to hold items; and an information device attached to the portable container and including a communication device for receiving information relating to a required change in the items held in the interior of the container;

wherein the information device includes a display device and wherein a message is displayed on the display device relating to the information received relating to a required change to the contents of the container.

54. The verification apparatus of claim 53, wherein the portable container has an interior adapted to hold prescription medication and wherein the information received relating to a required change in the items held in the container is a change in a prescription.

55. A labeling and tracking apparatus, comprising:

an information device adapted to be attached to an object to be labeled and tracked and including means for receiving and storing identification information therein;

an identification device related to a second object having identification device identification information stored therein and means for communicating the identification device identification information from the identification device to the information device to be stored therein;

wherein the information device is adapted to provide a response signal; and wherein the information device compares the information device identification information stored therein to the identification device identification information obtained from the identification device and provides the response signal if the identification device identification information corresponds to the stored information device identification information; and wherein one of the information device or the identification device includes means for generating a secret code, storing the secret code, and communicating the secret code to the other of the information device or the identification device, and wherein the other of the information device or the identification device includes means for receiving and storing the secret code, and wherein the information device compares the secret code stored therein to the secret code stored in the identification device and obtained therefrom and provides the response signal only if the secret codes in the information device and identification device correspond.

56. The labeling and tracking apparatus of claim 55, wherein the information device is attached to a container into which an object to be labeled and tracked is placed.

57. The labeling and tracking apparatus of claim 56, wherein the identification device identification information is patient information identifying the patient from which an object to be labeled and tracked is taken.

58. The labeling and tracking apparatus of claim 57, wherein the information device is attached to a container into which a sample collected from a patient is placed.

59. The labeling and tracking apparatus of claim 55, comprising additionally a workstation adapted to read the identification information stored in the information device.

60. The labeling and tracking apparatus of claim 55, comprising additionally an indicator to provide an indication connected to the information device and wherein the response signal provided by the information device controls the indicator to provide the indication if the identification device identification information corresponds to the stored information device identification information.

61. A labeling and tracking apparatus, comprising:
an information device adapted to be attached to an object to be labeled and tracked and including means for receiving and storing identification information therein; and
an identification device having identification device identification information stored therein and means for communicating the identification device identification information from the identification device to the information device to be stored therein;
wherein the information device is adapted to provide a response signal; and
wherein the information device compares the information device identification information stored therein to the identification device identification information obtained from the identification device and provides the response signal if the identification device identification information corresponds to the stored information device identification information; and
comprising additionally a locking mechanism connected to the information device and wherein the response signal provided by the information device controls the locking mechanism to unlock the locking mechanism when the identification device identification information corresponds to the stored information device identification information.

62. A labeling and tracking apparatus, comprising:
an information device adapted to be attached to an object to be labeled and tracked and including means for receiving and storing identification information therein; and
a first identification device having first identification device identification information stored therein and means for communicating the first identification device identification information from the first identification device to the information device to be stored therein;
a second identification device including second identification device identification information;
wherein the information device is adapted to provide a response signal and having information device identification information stored therein and adapted to obtain the second identification device identification information from the second identification device; and
wherein the information device compares the information device identification information stored therein to the second identification device identification information obtained from the second identification device and provides the response signal if the second identification device identification information corresponds to the stored information device identification information.

63. The labeling and tracking apparatus of claim 62, comprising additionally a portable locking mechanism connected to the information device and wherein the response signal provided by the information device controls the portable locking mechanism to unlock the locking mechanism when the second identification device identification information corresponds to the stored information device identification information.

64. The labeling and tracking apparatus of claim 62, comprising additionally an indicator to provide an indication connected to the information device and wherein the response signal provided by the information device controls the indicator to provide the indication if the second identification device identification information corresponds to the stored information device identification information.

65. A verification apparatus, comprising:
a container adapted to be opened and closed;
a sensor for detecting when the container is opened;
an information device attached to the container and including a clock for providing time information and memory and means for storing time information provided by the clock in the memory in response to the sensor when the container is opened.

66. The verification apparatus of claim 65, wherein the container includes medication therein.

67. The verification apparatus of claim 65, wherein the information device includes a communication device for transmitting the time information stored in memory corresponding to the time when the container is opened to a database.

68. A process for verifying information, comprising the steps of:
providing a dispensing workstation in communication with a database, a container, and an information device wherein the container has multiple individual compartments;
using the dispensing workstation to select information from the database;
dispensing goods corresponding to the selected information into the container;
communicating a dispensing signal containing the selected information including information device identification information to the information device;
transporting the goods in the container to an identification device;
communicating a verification signal containing identification device identification information from the identification device to the information device;
comparing the information device identification information and the identification device identification information; and
providing an indication if the information device identification information corresponds to the identification device identification information.

69. The process of claim 68, wherein portions of the selected information correspond to different individual compartments of the container.

70. The process of claim 69, wherein the individual compartments are lockable and comprising the additional step of unlocking individual compartments of the container when the selected information for an individual compartment corresponds to the identification information.

71. A verification method, comprising the steps of:
providing an identification device including identification device identification information;
providing a portable information device having information device identification information stored therein;
obtaining identification device identification information from the identification device into the portable information device;
comparing the information device identification information stored therein to the identification device identification information obtained from the identification device;
providing the response signal if the identification device identification information corresponds to the stored information device identification information; and displaying information stored in the information device.

72. The method of claim 71, wherein the step of comparing the information device identification information and the identification device identification information includes the step of communicating the information device identification information and the identification device identification information from the information device to a comparison system, performing the comparison in the comparison system to generate a comparison result signal, and communicating the comparison result signal from the comparison system to the information device, and wherein the information device provides the response signal in response to the comparison result signal.

73. The method of claim 71, wherein the step of obtaining identification device identification information from the identification device includes the steps of communicating the identification device identification information to the portable information device and receiving the identification device identification information into the portable information device.

74. The method of claim 71, wherein the step of obtaining identification device identification information includes the step of reading the identification device identification information from the identification device.

75. The method of claim 74, wherein the step of reading the identification device identification information includes the step of reading identification information provided on the identification device in bar code form.

76. The method of claim 71, comprising the additional steps of providing a portable locking mechanism and wherein the step of providing the response signal includes the step of controlling the portable locking mechanism to unlock the locking mechanism when the identification device identification information corresponds to the stored information device identification information.

77. The method of claim 76, wherein the step of controlling the portable locking mechanism includes the step of controlling access to an interior of a portable container.

78. The method of claim 76, wherein the step of controlling the portable locking mechanism includes the step of controlling a flow of fluid past a fluid flow control device.

79. The method of claim 71, wherein the step of providing the response signal includes the step of providing an indication if the identification device identification information corresponds to the stored information device identification information.

80. The method of claim 79, wherein the indication is selected from the group of indications consisting of visual and audible indications.

81. The method of claim 79, comprising the additional step of activating an alert indication when the information device identification information does not correspond to the identification device identification information.

82. The method of claim 71, comprising the additional step of modifying the information device identification information stored in the information device.

83. The method of claim 71, comprising the additional step of activating an alert indication when the information device identification information does not correspond to the identification device identification information.

84. The method of claim 71, wherein the identification device is an object identification device and wherein the information device identification information and the identification device identification information identify an object which must be identified for the response signal to be provided.

85. The method of claim 84, wherein the identification device is a patient identification device and wherein the information device identification information and the identification device identification information identify a patient which must be identified for the response signal to be provided.

86. The method of claim 84, wherein the identification device is a worker identification device and wherein the information device identification information and the identification device identification information identify a worker which must be identified for the response signal to be provided.

87. The method of claim 71, comprising the additional steps of providing a second identification device including second identification device identification information, obtaining the second identification device identification information from the second identification device into the information device, comparing the second identification device identification information to second information device identification information stored in the information device, and providing the response signal if the second identification device identification information corresponds to the stored second information device identification information.

88. The method of claim 71, comprising the additional step of attaching a container to the information device.

89. The method of claim 88, comprising the additional step of placing an IV bag in the container.

90. The method of claim 88, comprising the additional step of placing a medical sample tube in the container.

91. The method of claim 88, comprising the additional step of placing a plurality of personal items in the container.

92. The method of claim 88, comprising the additional step of transmitting information about the contents of the interior of the container to the information device.

93. The method of claim 88, comprising the additional steps of detecting when the container is opened and storing information in the information device indicating that the container was opened.

94. The method of claim 93, comprising the additional step of transmitting the information stored in memory indicating that the container was opened to a database.

95. The method of claim 93, comprising the additional steps of providing time information and storing time information in the information device when the container is opened.

96. The method of claim 95, comprising the additional step of transmitting the time information stored in memory when the container is opened to a database.

97. The method of claim 88, wherein the container includes a plurality of distinct interior sections.

98. The method of claim 97, wherein the information device includes stored information relating to selected interior sections of the container.

99. The method of claim 98, wherein the stored information relating to selected interior sections of the container is identification information and comprising the additional step of comparing the stored identification information relating to the selected interior sections of the container to the identification information obtained from the identification device and providing selected response signals when the identification information relating to selected interior sections of the containers corresponds to the identification information obtained from the identification device.

100. The method of claim 99, wherein the plurality of interior sections have separate locking mechanisms associated therewith, and wherein the step of providing selected response signals includes the step of unlocking access to selected ones of the plurality of interior sections of the container.

101. The method of claim 99, wherein the step of providing selected response signals includes the step of providing selected indications associated with selected ones of the plurality of interior sections of the container.

102. The method of claim 88, comprising the additional step of receiving information into the information device relating to a required change to the contents of the container.

103. The method of claim 102, wherein the container has an interior adapted to hold prescription medication and wherein the information received relating to a required change to the contents of the container is a change in a prescription.

104. The method of claim 102, comprising the additional step of displaying a message relating to the information received relating to a required change to the contents of the container.

105. The method of claim 102, wherein the step of providing the response signal is disabled in response to the receipt of the information relating to a required change to the contents of the container.

106. The method of claim 71 comprising additionally the steps of providing an infusion pump connected to the information device and enabling operation of the infusion pump in response to the response signal.

107. The method of claim 71, comprising additionally the steps of providing time information in the information device and storing time information in the information device in response to the providing of the response signal.

108. The method of claim 107, comprising additionally the step of transmitting the time information stored in the information device to a database.

109. The method of claim 71, comprising the additional step of storing in the identification device identification information obtained from the identification device.

110. The method of claim 109, comprising the additional step of transmitting the identification device identification information obtained from the identification device to a database.

111. The method of claim 110, comprising the additional step of transmitting the additional information obtained from the identification device and stored in the information device to a database.

112. The method of claim 109, wherein the identification device includes additional information stored therein and comprising the additional steps of obtaining the additional information from the identification device into the information device and storing the additional information in the information device.

113. A verification apparatus, comprising:
an identification device including identification device identification information;
a portable information device adapted to provide a response signal and having information device identification information stored therein and adapted to obtain identification device identification information from the identification device;
wherein the information device compares the information device identification information stored therein to the identification device identification information obtained from the identification device and provides the response signal if the identification device identification information corresponds to the stored information device identification information; and
wherein the information device includes a clock for providing time information and wherein the information device is connected to the clock and includes memory means for storing time information provided by the clock in response to the providing of the response signal.

114. The verification apparatus of claim 113, wherein the information device includes a communication device for transmitting the time information stored in the memory to a database.

* * * * *